(12) United States Patent
Belvedere et al.

(10) Patent No.: US 7,507,858 B2
(45) Date of Patent: Mar. 24, 2009

(54) HISTONE DEACETYLASE INHIBITORS

(75) Inventors: Sandro Belvedere, Verona (IT); Thomas A. Miller, Brookline, MA (US); David J. Witter, Norfolk, MA (US)

(73) Assignee: Merck & Co., Inc., Rahway, NJ (US)

( * ) Notice: Subject to any disclaimer, the term of this patent is extended or adjusted under 35 U.S.C. 154(b) by 110 days.

(21) Appl. No.: 11/629,448

(22) PCT Filed: Jul. 15, 2005

(86) PCT No.: PCT/US2005/025137

§ 371 (c)(1),
(2), (4) Date: Dec. 13, 2006

(87) PCT Pub. No.: WO2006/020004

PCT Pub. Date: Feb. 23, 2006

(65) Prior Publication Data

US 2008/0096920 A1    Apr. 24, 2008

Related U.S. Application Data

(60) Provisional application No. 60/589,079, filed on Jul. 19, 2004.

(51) Int. Cl.
*C07C 259/04* (2006.01)
(52) U.S. Cl. .................................................. 562/621
(58) Field of Classification Search .................. 562/621
See application file for complete search history.

(56) References Cited

U.S. PATENT DOCUMENTS

| 5,369,108 | A | 11/1994 | Breslow et al. |
| 5,700,811 | A | 12/1997 | Breslow et al. |
| 5,932,616 | A | 8/1999 | Breslow et al. |
| 6,087,367 | A | 7/2000 | Breslow et al. |
| 6,511,990 | B1 | 1/2003 | Breslow et al. |
| 2004/0029928 | A1 | 2/2004 | Hirata et al. |

FOREIGN PATENT DOCUMENTS

| WO | WO 02022577 | * | 3/2002 |
| WO | WO 03/087066 A1 | * | 10/2003 |

OTHER PUBLICATIONS

Kelly et al. Expert Opinion, Investigational Drugs, (2002) 11 (12), 1695-1713.*

* cited by examiner

*Primary Examiner*—D. Margaret Seaman
*Assistant Examiner*—Nizal S Chandrakumar
(74) *Attorney, Agent, or Firm*—Li Su; David A. Muthard

(57) ABSTRACT

This invention relates to iminodiacetic acid and diamine hydroxamic acid derivatives, that are inhibitors of histone deacetylase (HDAC), and are useful in the prevention and/or treatment of cellular proliferative diseases, for example cancer, autoimmune, allergic and inflammatory diseases, diseases of the central nervous system (CNS) such as neurodegenerative diseases, and in the prevention and/or treatment of restenosis.

11 Claims, No Drawings

HISTONE DEACETYLASE INHIBITORS

PRIORITY CLAIM

This application is a §371 National Stage Application of PCT/US2005/025137, filed on Jul. 15, 2005, which claims priority from U.S. Provisional Application Ser. No. 60/589,079, filed on Jul. 19, 2004.

BACKGROUND OF THE INVENTION

This invention relates to iminodiacetic acid and diamine hydroxamic acid derivatives, that are inhibitors of histone deacetylase (HDAC), and are useful in the prevention and/or treatment of cellular proliferative diseases, for example cancer, autoimmune, allergic and inflammatory diseases, diseases of the central nervous system (CNS) such as neurodegenerative diseases, and in the prevention and/or treatment of restenosis.

Compounds having a hydroxamic acid moiety have been shown to possess useful biological activities. For example, many peptidyl compounds possessing a hydroxamic acid moiety are known to inhibit matrix metalloproteinases (MMPs), which are a family of zinc endopeptidases. The MMPs play a key role in both physiological and pathological tissue degradation. Therefore, peptidyl compounds that have the ability to inhibit the action of MMPs show utility for the treatment or prophylaxis of conditions involving tissue breakdown and inflammation. Further, compounds having a hydroxamic acid moiety have been shown to inhibit histone deacetylases (HDACs), based at least in part on the zinc binding property of the hydroxamic acid group.

The inhibition of HDACs can repress gene expression, including expression of genes related to tumor suppression. Inhibition of histone deacetylase can lead to the histone deacetylase-mediated transcriptional repression of tumor suppressor genes. For example, inhibition of histone deacetylase can provide a method for treating cancer, hematological disorders, such as hematopoiesis, and genetic related metabolic disorders. More specifically, transcriptional regulation is a major event in cell differentiation, proliferation, and apoptosis. There are several lines of evidence that histone acetylation and deacetylation are mechanisms by which transcriptional regulation in a cell is achieved (Grunstein, M., Nature, 389: 349-52 (1997)). These effects are thought to occur through changes in the structure of chromatin by altering the affinity of histone proteins for coiled DNA in the nucleosome. There are five types of histones that have been identified. Histones H2A, H2B, H3 and H4 are found in the nucleosome and H1 is a linker located between nucleosomes. Each nucleosome contains two of each histone type within its core, except for H1, which is present singly in the outer portion of the nucleosome structure. It is believed that when the histone proteins are hypoacetylated, there is a greater affinity of the histone to the DNA phosphate backbone. This affinity causes DNA to be tightly bound to the histone and renders the DNA inaccessible to transcriptional regulatory elements and machinery.

The regulation of acetylated states occurs through the balance of activity between two enzyme complexes, histone acetyl transferase (HAT) and histone deacetylase (HDAC). The hypoacetylated state is thought to inhibit transcription of associated DNA. This hypoacetylated state is catalyzed by large multiprotein complexes that include HDAC enzymes. In particular, HDACs have been shown to catalyze the removal of acetyl groups from the chromatin core histones.

It has been shown in several instances that the disruption of HAT or HDAC activity is implicated in the development of a malignant phenotype. For instance, in acute promyelocytic leukemia, the oncoprotein produced by the fusion of PML and RAR alpha appears to suppress specific gene transcription through the recruitment of HDACs (Lin, R. J. et al., Nature 391:811-14 (1998)). In this manner, the neoplastic cell is unable to complete differentiation and leads to excess proliferation of the leukemic cell line.

U.S. Pat. Nos. 5,369,108, 5,932,616, 5,700,811, 6,087,367 and 6,511,990, the contents of which are hereby incorporated by reference, disclose hydroxamic acid derivatives useful for selectively inducing terminal differentiation, cell growth arrest or apoptosis of neoplastic cells. In addition to their biological activity as antitumor agents, these hydroxamic acid derivatives have recently been identified as useful for treating or preventing a wide variety of thioredoxin (TRX)-mediated diseases and conditions, such as inflammatory diseases, allergic diseases, autoimmune diseases, diseases associated with oxidative stress or diseases characterized by cellular hyperproliferation (U.S. application Ser. No. 10/369,094, filed Feb. 15, 2003, the entire content of which is hereby incorporated by reference). Further, these hydroxamic acid derivatives have been identified as useful for treating diseases of the central nervous system (CNS) such as neurodegenerative diseases and for treating brain cancer (See, U.S. application Ser. No. 10/273,401, filed Oct. 16, 2002, the entire content of which is hereby incorporated by reference).

The inhibition of HDAC by the hydroxamic acid containing compound suberoylanilide hydroxamic acid (SAHA) disclosed in the above referenced U.S. patents, is thought to occur through direct interaction with the catalytic site of the enzyme as demonstrated by X-ray crystallography studies (Finnin, M. S. et al., Nature 401:188-193 (1999)). The result of HDAC inhibition is not believed to have a generalized effect on the genome, but rather, only affects a small subset of the genome (Van Lint, C. et al., Gene Expression 5:245-53 (1996)). Evidence provided by DNA microarrays using malignant cell lines cultured with a HDAC inhibitor shows that there are a finite (1-2%) number of genes whose products are altered. For example, cells treated in culture with HDAC inhibitors show a consistent induction of the cyclin-dependent kinase inhibitor p21 (Archer, S. Shufen, M. Shei, A., Hodin, R. PNAS 95:6791-96 (1998)). This protein plays an important role in cell cycle arrest. HDAC inhibitors are thought to increase the rate of transcription of p21 by propagating the hyperacetylated state of histones in the region of the p21 gene, thereby making the gene accessible to transcriptional machinery. Genes whose expression is not affected by HDAC inhibitors do not display changes in the acetylation of regional associated histones (Dressel, U. et al., Anticancer Research 20(2A): 1017-22 (2000)).

Further, hydroxamic acid derivatives such as SAHA have the ability to induce tumor cell growth arrest, differentiation and/or apoptosis (Richon et al., Proc. Natl. Acad. Sci. USA, 93:5705-5708 (1996)). These compounds are targeted towards mechanisms inherent to the ability of a neoplastic cell to become malignant, as they do not appear to have toxicity in doses effective for inhibition of tumor growth in animals (Cohen, L. A. et al., Anticancer Research 19:4999-5006 (1999)).

In view of the wide variety of applications for compounds containing hydroxamic acid moieties, the development of new hydroxamic acid derivatives having improved properties, for example, increased potency or increased bioavailability is highly desirable.

SUMMARY OF THE INVENTION

This invention relates to iminodiacetic acid and diamine hydroxamic acid derivatives, that are inhibitors of histone deacetylase (HDAC), and are useful in the prevention and/or treatment of cellular proliferative diseases, for example cancer, autoimmune, allergic and inflammatory diseases, diseases of the central nervous system (CNS) such as neurodegenerative diseases, and in the prevention and/or treatment of restenosis.

In a first embodiment, the compounds of the invention may be illustrated by the Formula I:

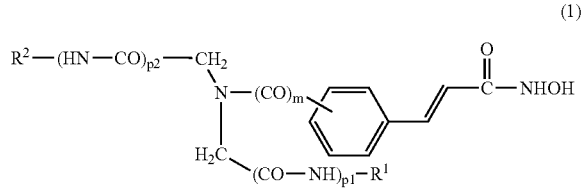

DETAILED DESCRIPTION OF THE INVENTION

The compounds of this invention are useful as HDAC inhibitors and are illustrated by a compound of Formula I:

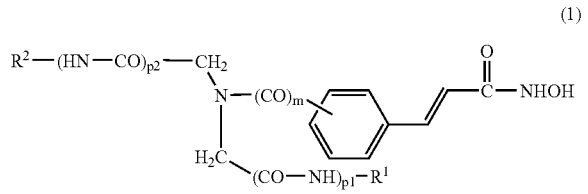

wherein m is 0 or 1;

$p^1$ and $p^2$ are independently of each other 0 or 1;

$R^1$ and $R^2$ are, independently of each other, unsubstituted or substituted and selected from $C_1$-$C_{10}$ alkyl, $C_2$-$C_{10}$ alkenyl, cycloalkyl, aryl, heterocyclyl, heteroaryl, $C_1$-$C_{10}$ alkyl-$C_2$-$C_{10}$ alkenyl, $C_1$-$C_{10}$ alkylcycloalkyl, $C_1$-$C_{10}$ alkylaryl, $C_1$-$C_{10}$ alkylheterocyclyl and $C_1$-$C_{10}$ alkylheteroaryl; or when $p_1$ and $p_2$ are both 0, $R^1$ and $R^2$ together with the —$CH_2$—N—$CH_2$— group to which they are attached can also represent a nitrogen-containing heterocyclic ring; or when at least one of $p^1$ or $p^2$ is not 0, $R^1$ or $R^2$ or both can also represent hydrogen or $C_1$-$C_{10}$ alkyl;

or a stereoisomer, enantiomer, racemate, pharmaceutically acceptable salt, solvate, hydrate or polymorph thereof.

In another embodiment of the instant invention, the compounds are illustrated by the compound of formula II:

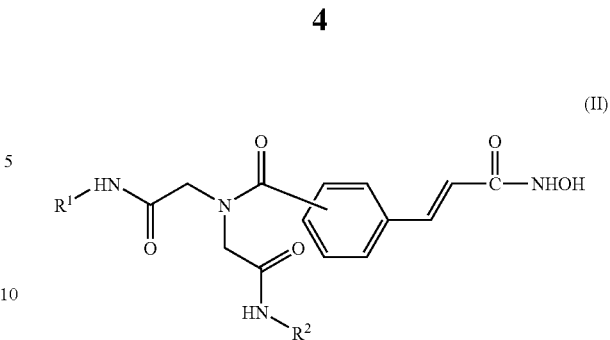

wherein $R^1$ and $R^2$ are as defined above for the compound of formula I, or a stereoisomer, enantiomer, racemate, pharmaceutically acceptable salt, solvate, hydrate or polymorph thereof.

In another embodiment of the instant invention, the compounds are illustrated by a compound of Formula III:

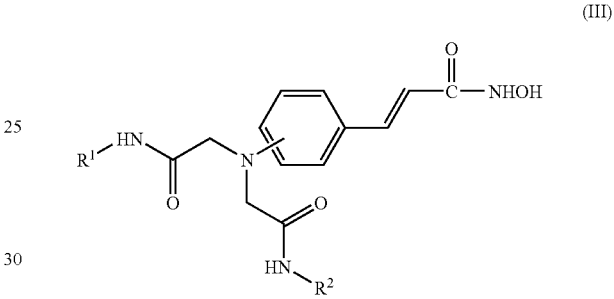

wherein $R^1$ and $R^2$ are as defined above for the compound of formula I, or a stereoisomer, enantiomer, racemate, pharmaceutically acceptable salt, solvate, hydrate or polymorph thereof.

In another embodiment of the instant invention, the compounds are illustrated by a compound of Formula IV:

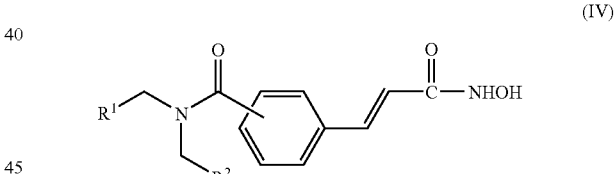

wherein $R^1$ and $R^2$ are as defined above for the compound of formula I, or a stereoisomer, enantiomer, racemate, pharmaceutically acceptable salt, solvate, hydrate or polymorph thereof.

In another embodiment of the instant invention, the compounds are illustrated by a compound of Formula V:

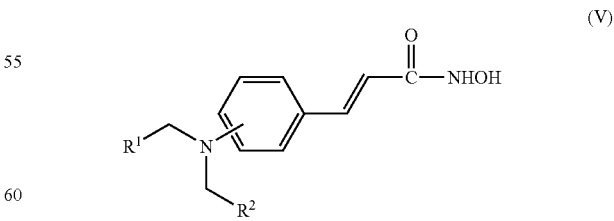

wherein $R^1$ and $R^2$ are as defined above for the compound of formula I, or a stereoisomer, enantiomer, racemate, pharmaceutically acceptable salt, solvate, hydrate or polymorph thereof.

Specific examples of the compounds of the instant invention include:

4-(2-Hydroxycarbamoyl-vinyl)-N,N-bis-phenylcarbamoyl-methyl-benzamide;

4-(2-Hydroxycarbamoyl-vinyl)-N,N-bis-(quinolin-8-ylcarbamoylmethyl)-benzamide;

3-[3-(Bis-phenylcarbamoylmethyl-amino)-phenyl]-N-hydroxy-acrylamide;

3-{3-[Bis-(quinolin-8-ylcarbamoylmethyl)-amino]-phenyl}-N-hydroxy-acrylamide;

3-{3-[Bis-(benzothiazol-2-ylcarbamoylmethyl)-amino]-phenyl}-N-hydroxy-acrylamide;

3-[4-(Bis-phenylcarbamoylmethyl-amino)-phenyl]-N-hydroxy-acrylamide; and

3-{4-[Bis-(quinolin-8-ylcarbamoylmethyl)-amino]-phenyl}-N-hydroxy-acrylamide;

or a stereoisomer, enantiomer, racemate, pharmaceutically acceptable salt, solvate, hydrate or polymorph thereof.

When any variable (e.g. $R^1$, $R^2$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. For example, in a ring system having two substituents, the two substitutents may be in an ortho, meta or para substitution pattern with respect to each other. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrases "optionally substituted" or "optionally substituted with one or more substituents" or "unsubstituted or substituted", used herein interchangeably, should be taken to be equivalent to the phrase "optionally substituted with at least one substituent" and in such cases in one embodiment will have from zero to three substituents. In one embodiment, the phrases "optionally substituted" or "optionally substituted with one or more substituents" or "unsubstituted or substituted" should be taken to mean the phrase "optionally substituted with one, two or three substituents".

As used herein, "alkyl" is intended to include both branched and straight-chain saturated aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, n-propyl, i-propyl, n-butyl, t-butyl, i-butyl, pentyl, hexyl, heptyl, octyl, nonyl, decyl, and so on. The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl and so on.

The term "alkylene" means a hydrocarbon diradical group having the specified number of carbon atoms. For example, "alkylene" includes —$CH_2$—, —$CH_2CH_2$— and the like.

The terms "alkylalkenyl" "alkylcycloalkyl", alkylaryl", alkylheterocyclyl" or alkylheteroaryl" mean an alkyl radical linked to an alkenyl, cycloalkyl, aryl, heterocyclyl or heteroaryl group, respectively. For example, in the phrase "$C_1$-$C_6$ alkylaryl" or "$C_1$-$C_6$ alkylheteroaryl" the term "$C_1$-$C_6$" refers to the alkyl portion of the moiety and does not describe the number of atoms in the aryl and heteroaryl portion of the moiety.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylenearyl. If aryl is taken to be phenyl, this definition would include phenyl itself as well as —$CH_2Ph$, —$CH_2CH_2Ph$, —$CH_2CH_2CH_2Ph$, $CH(CH_3)CH_2CH(CH_3)Ph$, and so on.

As used herein, "aryl" is intended to mean any stable monocyclic or bicyclic carbon ring of up to 7 atoms in each ring, wherein at least one ring is aromatic. Examples of such aryl elements include phenyl, naphthyl, fluorenyl, tetrahydronaphthyl, indanyl and biphenyl. In cases where the aryl substituent is bicyclic and one ring is non-aromatic, it is understood that attachment is via the aromatic ring.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" as used herein is intended to mean a 3- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrahydro analogs thereof. Further examples of "heterocyclyl" include, but are not limited to the following: azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

In an embodiment, the term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" in this embodiment therefore includes the above mentioned heteroaryls, as well as dihydro and tetrahydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

In another embodiment, heterocycle is selected from quinolinyl, isoquinolinyl, and thiazolyl.

As appreciated by those of skill in the art, "halo" or "halogen" as used herein is intended to include chloro, fluoro, bromo and iodo.

A "haloalkyl group" is an alkyl group of indicated number of carbon atoms, that is attached to one or more halogen atoms (e.g. one two, three, four, five or six halogen atoms), including chloro, fluoro, bromo and iodo. An example of a haloalkyl group is $CF_3$.

An "aryloxy group" is an aryl group that is attached to a compound via an oxygen (e.g., phenoxy).

"Alkoxy" (alkyloxy) represents either a cyclic or non-cyclic alkyl group of indicated number of carbon atoms attached through an oxygen bridge. "Alkoxy" or "alkyloxy" therefore encompasses the definitions of alkyl and cycloalkyl above. An example of an alkoxy group is $OCH_3$.

"Haloalkoxy" (haloalkyloxy") represents either a cyclic or non-cyclic-alkyl group of indicated number of carbon atoms attached through an oxygen bridge, which groups is attached to at least one halogen atom (e.g. one two, three, four, five or six halogen atoms), including chloro, fluoro, bromo and iodo. An example of a haloalkyloxy group is $OCF_3$.

An "arylalkoxy group" (arylalkyloxy) represents an arylalkyl group that is attached to a compound via an oxygen on the alkyl portion of the arylalkyl (e.g., phenylmethoxy).

An "arylamino group", represents an aryl group that is attached to a compound via a nitrogen.

As used herein, an "arylalkylamino group" is an arylalkyl group that is attached to a compound via a nitrogen on the alkyl portion of the arylalkyl.

As used herein, many moieties or groups are referred to as being either "substituted or unsubstituted" or "optionally substituted". When a moiety is referred to as substituted, it denotes that any portion of the moiety that is known to one skilled in the art as being available for substitution can be substituted. The phrase "optionally substituted with one or more substituents" means, in one embodiment, "zero to five substituents", and in other embodiments, one substituent, two substituents, three substituents, four substituents or five substituents. For example, the substitutable group can be a hydrogen atom that is replaced with a group other than hydrogen (i.e., a substituent group). Multiple substituent groups can be present. When multiple substituents are present, the substituents can be the same or different and substitution can be at any of the substitutable sites. Such means for substitution are well known in the art. For purposes of exemplification, which should not be construed as limiting the scope of this invention, some examples of groups that are substituents (designated herein as "$R^{sub}$") are: $C_1$-$C_{10}$ alkyl groups, e.g. $CH_3$, $CH(CH_3)_2$, $C(CH_3)_3$ etc (which can also be substituted with one or more substituents); $C_1$-$C_{10}$ haloalkyl groups, e.g. $CF_3$, (which can also be substituted with one or more substituents); $C_1$-$C_{10}$ alkyloxy groups, e.g. $OCH_3$, (which can be substituted); $C_1$-$C_{10}$ haloalkyloxy groups, e.g. $OCF_3$; a halogen or halo group (F, Cl, Br, I); hydroxyl; nitro; oxo; —CN; —COH; —COOH; amino; azido; N-alkylamino or N,N-dialkylamino (in which the alkyl groups can also be substituted); N-arylamino or N,N-diarylamino (in which the aryl groups can also be substituted); aryl (e.g. phenyl), esters (—C(O)—OR, where R can be a group such as alkyl, aryl, etc., which can be substituted); aryl (which can be substituted); cycloalkyl (which can be substituted) alkylaryl (which can be substituted); alkylheterocyclyl (which can be substituted); alkylcycloalkyl (which can be substituted), and aryloxy (e.g. —OPh).

In one embodiment of the instant invention, $p^1$, $p^2$ and m are each 1 in the compounds of formula I. In accordance with this embodiment, the compounds of formula I may be represented by formula II. In another embodiment of the instant invention, $p^1$ and $p^2$ are each 1 and m is 0 in the compounds of formula I. In accordance with this embodiment, the compounds of formula I may be represented by formula III. In another embodiment of the instant invention, $p^1$ and $p^2$ are each 0 and m is 1 in the compounds of formula I. In accordance with this embodiment, the compounds of formula I may be represented by formula IV. In another embodiment of the instant invention, $p^1$, $p^2$ and m are each 0 in the compounds of formula I. In accordance with this embodiment, the compounds of formula I may be represented by formula V.

In one embodiment of the instant invention, $R^1$ and/or $R^2$ in the compounds of formula I are unsubstituted. In another embodiment, $R^1$ and/or $R^2$ in the compounds of formula I are substituted with one, two or three substituents independently selected from $R^{sub}$, wherein $R^{sub}$ is a substitutent selected from $C_1$-$C_{10}$ alkyl, $C_1$-$C_{10}$ haloalkyl, $C_2$-$C_{10}$ alkenyl, cycloalkyl, aryl (e.g. phenyl), heterocyclyl, heteroaryl, $C_1$-$C_{10}$ alkyl-$C_2$-$C_{10}$ alkenyl, $C_1$-$C_{10}$ alkylcycloalkyl, $C_1$-$C_{10}$ alkylaryl, $C_1$-$C_{10}$ alkylheterocyclyl, $C_1$-$C_{10}$ alkylheteroaryl, halogen, hydroxy, $C_1$-$C_{10}$ alkyloxy, $C_1$-$C_{10}$ haloalkyloxy, aryloxy, nitro, oxo, —CN, —C(=O)H, —C(=O)OH, amino, N—$C_1$-$C_{10}$ alkylamino, N,N-di $C_1$-$C_{10}$ alkylamino, N-arylamino, N,N-diarylamino, N—$C_1$-$C_{10}$ alkyl-N-arylamino, azido, and C(=O)OR wherein R is aryl or $C_1$-$C_{10}$ alkyl. In another embodiment, $R^{sub}$ in the compounds of formula I is independently selected from $C_1$-$C_4$ alkyl, $C_1$-$C_4$ haloalkyl, $C_1$-$C_4$ haloalkyloxy, $C_1$-$C_4$ alkyloxy, aryl (e.g. phenyl), halogen and nitro. Specific non-limiting examples of such substituents include one, two or three substituents selected from Cl, Br, $CF_3$, $OCH_3$, Ph, $NO_2$, OPh, $CH_3$, $CH(CH_3)_2$, $C(CH_3)_3$ and $OCF_3$.

In one embodiment of the instant invention, $R^1$ and/or $R^2$ in the compounds of formula II are unsubstituted. In another embodiment, $R^1$ and/or $R^2$ in the compounds of formula II are substituted with one, two or three substituents independently selected from $R^{sub}$, wherein $R^{sub}$ is a substitutent selected from $C_1$-$C_{10}$ alkyl, $C_1$-$C_{10}$ haloalkyl, $C_2$-$C_{10}$ alkenyl, cycloalkyl, aryl (e.g. phenyl), heterocyclyl, heteroaryl, $C_1$-$C_{10}$ alkyl-$C_2$-$C_{10}$ alkenyl, $C_1$-$C_{10}$ alkylcycloalkyl, $C_1$-$C_{10}$ alkylaryl, $C_1$-$C_{10}$ alkylheterocyclyl, $C_1$-$C_{10}$ alkylheteroaryl, halogen, hydroxy, $C_1$-$C_{10}$ alkyloxy, $C_1$-$C_{10}$ haloalkyloxy, aryloxy, nitro, oxo, —CN, —C(=O)H, —C(=O)OH, amino, N—$C_1$-$C_{10}$ alkylamino, N,N-di $C_1$-$C_{10}$ alkylamino, N-arylamino, N,N-diarylamino, N—$C_1$-$C_{10}$ alkyl-N-arylamino, azido, and C(=O)OR wherein R is aryl or $C_1$-$C_{10}$ alkyl. In another embodiment, $R^{sub}$ in the compounds of formula II is independently selected from $C_1$-$C_4$ alkyl, $C_1$-$C_4$ haloalkyl, $C_1$-$C_4$ haloalkyloxy, $C_1$-$C_4$ alkyloxy, aryl (e.g. phenyl), halogen and nitro. Specific non-limiting examples of such substituents include one, two or three substituents selected from Cl, Br, $CF_3$, $OCH_3$, Ph, $NO_2$, OPh, $CH_3$, $CH(CH_3)_2$, $C(CH_3)_3$ and $OCF_3$.

In one embodiment of the instant invention, $R^1$ and/or $R^2$ in the compounds of formula In are unsubstituted. In another embodiment, $R^1$ and/or $R^2$ in the compounds of formula III are substituted with one, two or three substituents independently selected from $R^{sub}$, wherein $R^{sub}$ is a substitutent selected from $C_1$-$C_{10}$ alkyl, $C_1$-$C_{10}$ haloalkyl, $C_2$-$C_{10}$ alkenyl, cycloalkyl, aryl (e.g. phenyl), heterocyclyl, heteroaryl, $C_1$-$C_{10}$ alkyl-$C_2$-$C_{10}$ alkenyl, $C_1$-$C_{10}$ alkylcycloalkyl, $C_1$-$C_{10}$ alkylaryl, $C_1$-$C_{10}$ alkylheterocyclyl, $C_1$-$C_{10}$ alkylheteroaryl, halogen, hydroxy, $C_1$-$C_{10}$ alkyloxy, $C_1$-$C_{10}$ haloalkyloxy, aryloxy, nitro, oxo, —CN, —C(=O)H, —C(=O)OH, amino, N—$C_1$-$C_{10}$ alkylamino, N,N-di $C_1$-$C_{10}$ alkylamino, N-arylamino, N,N-diarylamino, N—$C_1$-$C_{10}$ alkyl-N-arylamino, azido, and C(=O)OR wherein R is aryl or $C_1$-$C_{10}$ alkyl. In another embodiment, $R^{sub}$ in the compounds of formula III is independently selected from $C_1$-$C_4$ alkyl, $C_1$-$C_4$ haloalkyl, $C_1$-$C_4$ haloalkyloxy, $C_1$-$C_4$ alkyloxy, aryl (e.g. phenyl), halogen and nitro. Specific non-limiting examples of such substituents include one, two or three substituents selected from Cl, Br, $CF_3$, $OCH_3$, Ph, $NO_2$, OPh, $CH_3$, $CH(CH_3)_2$, $C(CH_3)_3$ and $OCF_3$.

In one embodiment of the instant invention, $R^1$ and/or $R^2$ in the compounds of formula IV are unsubstituted. In another embodiment, $R^1$ and/or $R^2$ in the compounds of formula IV are substituted with one, two or three substituents independently selected from $R^{sub}$, wherein $R^{sub}$ is a substitutent selected from $C_1$-$C_{10}$ alkyl, $C_1$-$C_{10}$ haloalkyl, $C_2$-$C_{10}$ alkenyl, cycloalkyl, aryl (e.g. phenyl), heterocyclyl, heteroaryl, $C_1$-$C_{10}$ alkyl-$C_2$-$C_{10}$ alkenyl, $C_1$-$C_{10}$ alkylcycloalkyl, $C_1$-$C_{10}$ alkylaryl, $C_1$-$C_{10}$ alkylheterocyclyl, $C_1$-$C_{10}$ alkylheteroaryl, halogen, hydroxy, $C_1$-$C_{10}$ alkyloxy, $C_1$-$C_{10}$ haloalkyloxy, aryloxy, nitro, oxo, —CN, —C(=O)H, —C(=O)OH, amino, N—$C_1$-$C_{10}$ alkylamino, N,N-di $C_1$-$C_{10}$ alkylamino, N-arylamino, N,N-diarylamino, N—$C_1$-$C_{10}$ alkyl-N-arylamino, azido, and C(=O)OR wherein R is aryl or $C_1$-$C_{10}$ alkyl. In another embodiment, $R^{sub}$ in the compounds of formula IV is independently selected from $C_1$-$C_4$ alkyl, $C_1$-$C_4$ haloalkyl, $C_1$-$C_4$ haloalkyloxy, $C_1$-$C_4$ alkyloxy, aryl (e.g. phenyl), halogen and nitro. Specific non-limiting examples of such substituents include one, two or three substituents selected from Cl, Br, $CF_3$, $OCH_3$, Ph, $NO_2$, OPh, $CH_3$, $CH(CH_3)_2$, $C(CH_3)_3$ and $OCF_3$.

In one embodiment of the instant invention, $R^1$ and/or $R^2$ in the compounds of formula V are unsubstituted. In another embodiment, $R^1$ and/or $R^2$ in the compounds of formula V are substituted with one, two or three substituents independently selected from $R^{sub}$, wherein $R^{sub}$ is a substitutent selected from $C_1$-$C_{10}$ alkyl, $C_1$-$C_{10}$ haloalkyl, $C_2$-$C_{10}$ alkenyl, cycloalkyl, aryl (e.g. phenyl), heterocyclyl, heteroaryl, $C_1$-$C_{10}$ alkyl-$C_2$-$C_{10}$ alkenyl, $C_1$-$C_{10}$ alkylcycloalkyl, $C_1$-$C_{10}$ alkylaryl, $C_1$-$C_{10}$ alkylheterocyclyl, $C_1$-$C_{10}$ alkylheteroaryl, halogen, hydroxy, $C_1$-$C_{10}$ alkyloxy, $C_1$-$C_{10}$ haloalkyloxy, aryloxy, nitro, oxo, —CN, —C(=O)H, —C(=O)OH, amino, N—$C_1$-$C_{10}$ alkylamino, N,N-di $C_1$-$C_{10}$ alkylamino, N-arylamino, N,N-diarylamino, N—$C_1$-$C_{10}$ alkyl-N-arylamino, azido, and C(=O)OR wherein R is aryl or $C_1$-$C_{10}$ alkyl. In another embodiment, $R^{sub}$ in the compounds of formula V is independently selected from $C_1$-$C_4$ alkyl, $C_1$-$C_4$ haloalkyl, $C_1$-$C_4$ haloalkyloxy, $C_1$-$C_4$ alkyloxy, aryl (e.g. phenyl), halogen and nitro. Specific non-limiting examples of such substituents include one, two or three substituents selected from Cl, Br, $CF_3$, $OCH_3$, Ph, $NO_2$, OPh, $CH_3$, $CH(CH_3)_2$, $C(CH_3)_3$ and $OCF_3$.

In another embodiment of the instant invention, $R^1$ and $R^2$ in the compounds of formula I are independently of each other unsubstituted or substituted and selected from phenyl, naphthyl, fluorenyl, biphenyl, benzyl, —$CH_2CH_2Ph$, —$CH_2CH_2CH_2Ph$, cyclopropyl, cyclohexyl, quinolinyl, isoquinolinyl, —$CH_2$-quinolinyl, —$CH_2$-isoquinolinyl, thiazolyl, benzothiazolyl, $CH(Ph)_2$ and $C_1$-$C_{10}$ alkyl. In another embodiment, when $R^1$ and/or $R^2$ are substituted, the substituent comprises one, two or three groups independently selected from $R^{sub}$, wherein $R^{sub}$ is selected from $C_1$-$C_4$ alkyl, $C_1$-$C_4$ haloalkyl, $C_1$-$C_4$ haloalkyloxy, $C_1$-$C_4$ alkyloxy, aryl, halogen and nitro. Specific non-limiting examples of such substituents include Cl, Br, $CF_3$, $OCH_3$, Ph, $NO_2$, OPh, $CH_3$, $CH(CH_3)_2$, $C(CH_3)_3$ and $OCF_3$.

In another embodiment of the instant invention, $R^1$ and $R^2$ in the compounds of formula II are independently of each other unsubstituted or substituted and selected from phenyl, naphthyl, fluorenyl, biphenyl, benzyl, —$CH_2CH_2Ph$, —$CH_2CH_2CH_2Ph$, cyclopropyl, cyclohexyl, quinolinyl, isoquinolinyl, —$CH_2$-quinolinyl, —$CH_2$-isoquinolinyl, thiazolyl, benzothiazolyl, $CH(Ph)_2$ and $C_1$-$C_{10}$ alkyl. In another embodiment, when R¹ and/or R² are substituted, the substituent comprises one, two or three groups independently selected from $R^{sub}$, wherein $R^{sub}$ is selected from $C_1$-$C_4$ alkyl, $C_1$-$C_4$ haloalkyl, $C_1$-$C_4$ haloalkyloxy, $C_1$-$C_4$ alkyloxy, aryl, halogen and nitro. Specific non-limiting examples of such substituents include Cl, Br, $CF_3$, $OCH_3$, Ph, $NO_2$, OPh, $CH_3$, $CH(CH_3)_2$, $C(CH_3)_3$ and $OCF_3$.

In another embodiment of the instant invention, R¹ and R² in the compounds of formula III are independently of each other unsubstituted or substituted and selected from phenyl, naphthyl, fluorenyl, biphenyl, benzyl, —$CH_2CH_2$Ph, —$CH_2CH_2CH_2$Ph, cyclopropyl, cyclohexyl, quinolinyl, isoquinolinyl, —$CH_2$-quinolinyl, —$CH_2$-isoquinolinyl, thiazolyl, benzothiazolyl, $CH(Ph)_2$ and $C_1$-$C_{10}$ alkyl. In another embodiment, when R¹ and/or R² are substituted, the substituent comprises one, two or three groups independently selected from $R^{sub}$, wherein $R^{sub}$ is selected from $C_1$-$C_4$ alkyl, $C_1$-$C_4$ haloalkyl, $C_1$-$C_4$ haloalkyloxy, $C_1$-$C_4$ alkyloxy, aryl, halogen and nitro. Specific non-limiting examples of such substituents include Cl, Br, $CF_3$, $OCH_3$, Ph, $NO_2$, OPh, $CH_3$, $CH(CH_3)_2$, $C(CH_3)_3$ and $OCF_3$.

In another embodiment of the instant invention, R¹ and R² in the compounds of formula IV are independently of each other unsubstituted or substituted and selected from phenyl, naphthyl, fluorenyl, biphenyl, benzyl, —$CH_2CH_2$Ph, —$CH_2CH_2CH_2$Ph, cyclopropyl, cyclohexyl, quinolinyl, isoquinolinyl, —$CH_2$-quinolinyl, —$CH_2$-isoquinolinyl, thiazolyl, benzothiazolyl, $CH(Ph)_2$ and $C_1$-$C_{10}$ alkyl. In another embodiment, when R¹ and/or R² are substituted, the substituent comprises one, two or three groups independently selected from $R^{sub}$, wherein $R^{sub}$ is selected from $C_1$-$C_4$ alkyl, $C_1$-$C_4$ haloalkyl, $C_1$-$C_4$ haloalkyloxy, $C_1$-$C_4$ alkyloxy, aryl, halogen and nitro. Specific non-limiting examples of such substituents include Cl, Br, $CF_3$, $OCH_3$, Ph, $NO_2$, OPh, $CH_3$, $CH(CH_3)_2$, $C(CH_3)_3$ and $OCF_3$.

In another embodiment of the instant invention, R¹ and R² in the compounds of formula V are independently of each other unsubstituted or substituted and selected from phenyl, naphthyl, fluorenyl, biphenyl, benzyl, —$CH_2CH_2$Ph, —$CH_2CH_2CH_2$Ph, cyclopropyl, cyclohexyl, quinolinyl, isoquinolinyl, —$CH_2$-quinolinyl, —$CH_2$-isoquinolinyl, thiazolyl, benzothiazolyl, $CH(Ph)_2$ and $C_1$-$C_{10}$ alkyl. In another embodiment, when R¹ and/or R² are substituted, the substituent comprises one, two or three groups independently selected from $R^{sub}$, wherein $R^{sub}$ is selected from $C_1$-$C_4$ alkyl, $C_1$-$C_4$ haloalkyl, $C_1$-$C_4$ haloalkyloxy, $C_1$-$C_4$ alkyloxy, aryl, halogen and nitro. Specific non-limiting examples of such substituents include Cl, Br, $CF_3$, $OCH_3$, Ph, $NO_2$, OPh, $CH_3$, $CH(CH_3)_2$, $C(CH_3)_3$ and $OCF_3$.

In another embodiment of the instant invention, R¹ and R² in the compounds of formula I, II, III, IV or V are independently of each other unsubstituted or substituted and selected from phenyl, quinolinyl and benzothiazol.

In another embodiment of the instant invention, R¹ and R² in the compounds of formula I, II, III, IV or V are independently of each other and selected from phenyl, quinolinyl and benzothiazol.

In the compounds of formulas I-V, the substituents can be in any position with respect to each other, i.e. ortho (1,2 substitution), meta (1,3 substitution) or para (1,4 substitution) to each other.

In one embodiment, the compounds of Formula I are illustrated by a compound of Formula IA (meta substitution). In another embodiment, the compounds of Formula I are illustrated by a compound of Formula IB (para substitution).

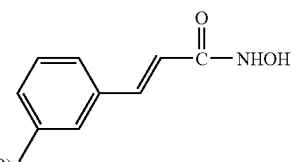
(IA)

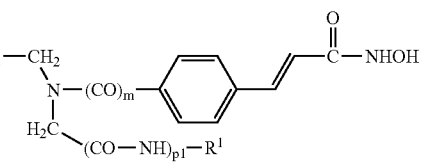
(IB)

In one embodiment, the compounds of Formula II are illustrated by a compound of Formula IIA (meta substitution). In another embodiment, the compounds of Formula II are illustrated by a compound of Formula IIB (para substitution).

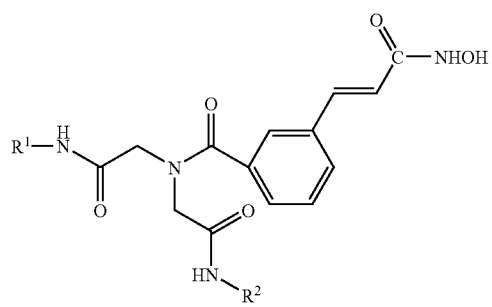
(IIA)

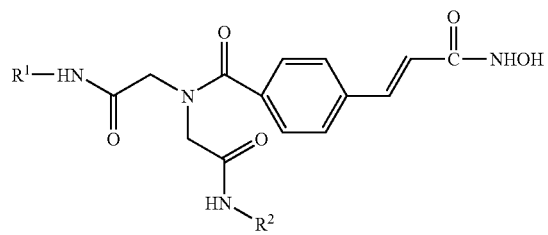
(IIB)

In one embodiment, the compounds of Formula III are illustrated by a compound of Formula IIIA (meta substitution). In another embodiment, the compounds of Formula III are illustrated by a compound of Formula IIIb (para substitution).

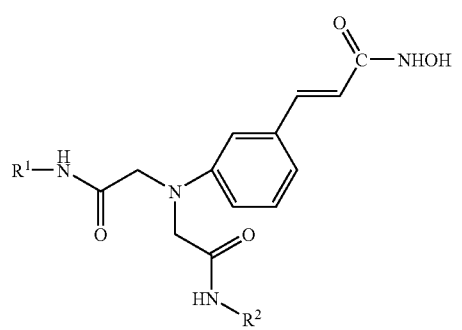
(IIIA)

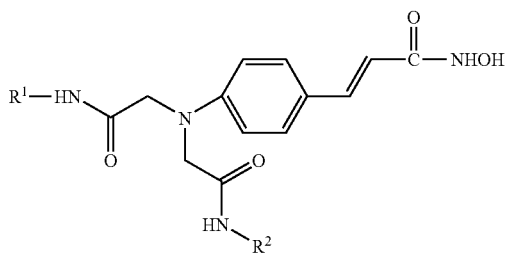
(IIIB)

In one embodiment, the compounds of Formula IV are illustrated by a compound of Formula IV (meta substitution). In another embodiment, the compounds of Formula IV are illustrated by a compound of Formula IV (para substitution).

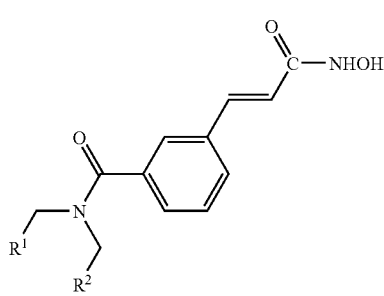
(IVA)
(IVB)

In one embodiment, the compounds of Formula V are illustrated by a compound of Formula VA (meta substitution). In another embodiment, the compounds of Formula V are illustrated by a compound of Formula VB (para substitution).

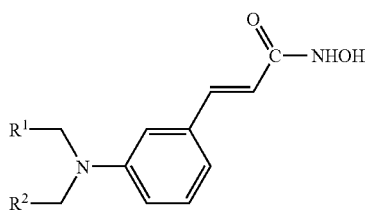
(VA)

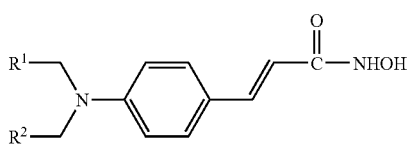
(VB)

In another embodiment, the present invention includes enantiomers of the compounds of formula I. In yet another embodiment, the present invention includes racemates of the compounds of formula I.

Included in the instant invention is the free form of compounds of Formula I, as well as the pharmaceutically acceptable salts and stereoisomers thereof. Some of the specific compounds exemplified herein are the protonated salts of amine compounds. The term "free form" refers to the amine compounds in non-salt form. The encompassed pharmaceutically acceptable salts not only include the salts exemplified for the specific compounds described herein, but also all the typical pharmaceutically acceptable salts of the free form of compounds of Formula I. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the formulas of the invention, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When the HDAC inhibitors of the present invention contain one chiral center, the compounds exist in two enantiomeric forms and the present invention includes both enantiomers and mixtures of enantiomers, such as the specific 50:50 mixture referred to as a racemic mixtures. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

Designation of a specific absolute configuration at a chiral carbon of the compounds of the invention is understood to mean that the designated enantiomeric form of the compounds is in enantiomeric excess (ee) or in other words is substantially free from the other enantiomer. For example, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. Enantiomeric excess, as used herein, is the presence of a particular enantiomer at greater than 50%. For example, the enantiomeric excess can be about 60% or more, such as about 70% or more, for example about 80% or more, such as about 90% or more. In a particular embodiment when a specific absolute configuration is designated, the enantiomeric excess of depicted compounds is at least about 90%. In a more particular embodiment, the enantiomeric excess of the compounds is at least about 95%, such as at least about 97.5%, for example, at least 99% enantiomeric excess.

When a compound of the present invention has two or more chiral carbons it can have more than two optical isomers and can exist in diastereoisomeric forms. For example, when there are two chiral carbons, the compound can have up to 4 optical isomers and 2 pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs may be separated by methods known to those skilled in the art, for example chromatography or crystallization and the individual enantiomers within each pair may be separated as described above. The present invention includes each diastereoisomer of such compounds and mixtures thereof.

The hydroxamic acid derivatives described herein can, as noted above, be prepared in the form of their pharmaceutically acceptable salts.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

When the compound of the present invention is acidic, suitable "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N[1]-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The active compounds disclosed can, as noted above, also be prepared in the form of their hydrates. The term "hydrate" includes but is not limited to hemihydrate, monohydrate, dihydrate, trihydrate, tetrahydrate and the like.

The active compounds disclosed can, as noted above, also be prepared in the form of a solvate with any organic or inorganic solvent, for example alcohols such as methanol, ethanol, propanol and isopropanol, ketones such as acetone, aromatic solvents and the like.

The active compounds disclosed can also be prepared in any solid or liquid physical form. For example, the compound can be in a crystalline form, in amorphous form, and have any particle size. Furthermore, the compound particles may be micronized, or may be agglomerated, particulate granules, powders, oils, oily suspensions or any other form of solid or liquid physical form.

The compounds of the present invention may also exhibit polymorphism. This invention further includes different polymorphs of the compounds of the present invention. The term "polymorph" refers to a particular crystalline state of a substance, having particular physical properties such as X-ray diffraction, IR spectra, melting point, and the like.

This invention is also intended to encompass pro-drugs of the hydroxamic acid derivatives disclosed herein. A prodrug of any of the compounds can be made using well known pharmacological techniques.

This invention, in addition to the above listed compounds, is intended to encompass the use of homologs and analogs of such compounds. In this context, homologs are molecules having substantial structural similarities to the above-described compounds and analogs are molecules having substantial biological similarities regardless of structural similarities.

The compounds of this invention may be prepared by employing reactions as shown in the following schemes, in addition to other standard manipulations that are known in the literature or exemplified in the experimental procedures. The illustrative schemes below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of Formula I hereinabove.

SCHEMES

The compounds of the present invention can be synthesized as exemplified in Schemes 1-4, which illustrate the synthesis of iminodiacetic-acid derived tertiary amine hydroxamic acids (compounds of Formulas II and III). Similar methodologies known to a person skilled in the art can be used to prepare the diamine compounds of Formulas IV and V.

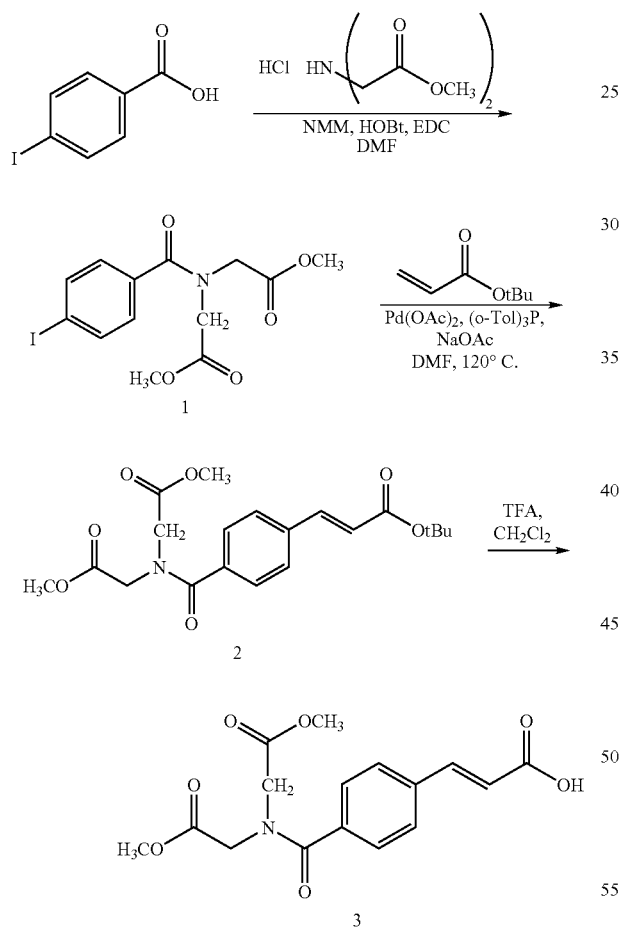

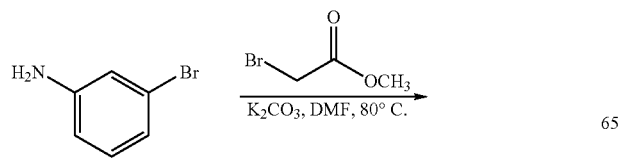

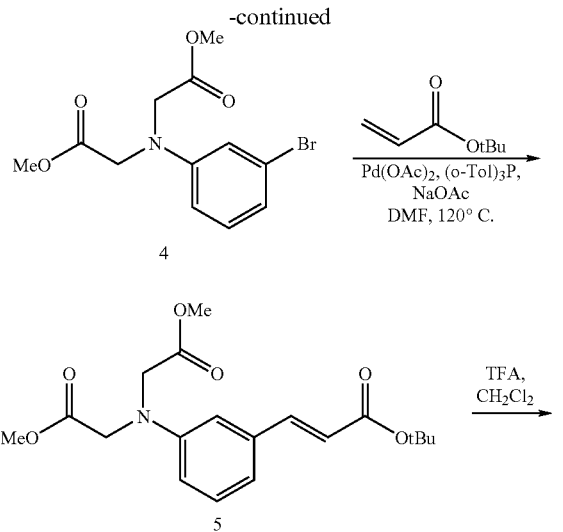

SCHEME 4

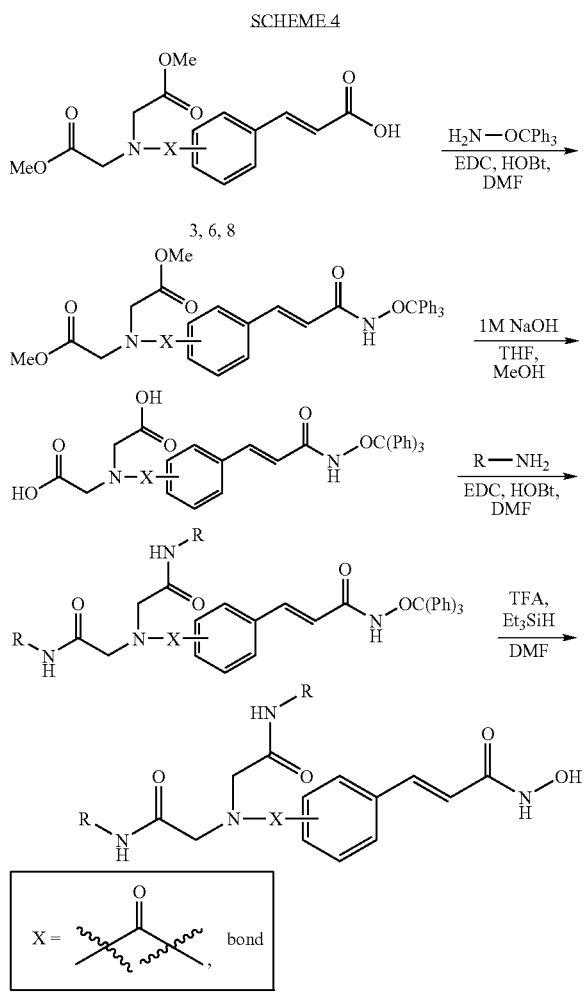

UTILITY

The invention also relates to methods of using the hydroxamic acid derivatives described herein. As demonstrated herein, the hydroxamic acid derivatives of the present invention are useful for the treatment of cancer. In addition, there is a wide range of other diseases for which hydroxamic acid derivatives have been found useful. Non-limiting examples are thioredoxin (TRX)-mediated diseases as described herein, diseases of the central nervous system (CNS) as described herein, and treatment of restenosis by providing a stent device comprising the hydroxamic acid derivatives as described herein.

As demonstrated herein, the hydroxamic acid derivatives of the present invention are useful for the treatment of cancer.

Accordingly, in one embodiment, the instant invention relates to a method of treating cancer in a subject in need of treatment comprising administering to said subject a therapeutically effective amount of the hydroxamic acid derivatives described herein.

In another embodiment, the instant invention relates to the use of any one or more of the hydroxamic acid derivatives disclosed herein in the preparation of a medicament. In another embodiment, the instant invention relates to the use of any one or more of the hydroxamic acid derivatives disclosed herein in the preparation of a medicament for the treatment of cancer in a subject in need of such treatment.

The compounds, compositions and methods provided herein are particularly deemed useful for the treatment of cancer including solid tumors such as skin, breast, brain, cervical carcinomas, testicular carcinomas, etc.

The term "cancer" refers to any cancer caused by the proliferation of neoplastic cells, such as solid tumors, neoplasms, carcinomas, sarcomas, leukemias, lymphomas and the like. For example, cancers include, but are not limited to: leukemias including acute leukemias and chronic leukemias such as acute lymphocytic leukemia (ALL), Acute myeloid leukemia (AML), chronic lymphocytic leukemia (CLL), chronic myelogenous leukemia (CML) and Hairy Cell Leukemia; lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), Hodgkin's disease and non-Hodgkin's lymphomas, large-cell lymphomas, diffuse large B-cell lymphoma (DLBCL); Burkitt's lymphoma; primary central nervous system (CNS) lymphoma; multiple myeloma; childhood solid tumors such as brain tumors, neuroblastoma, retinoblastoma, Wilm's tumor, bone tumors, and soft-tissue sarcomas, common solid tumors of adults such as head and neck cancers (e.g., oral, laryngeal and esophageal), genito urinary cancers (e.g., prostate, bladder, renal, uterine, ovarian, testicular, rectal and colon), lung cancer, breast cancer.

In a further embodiment, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

As demonstrated herein, the hydroxamic acid derivatives of the present invention are useful for the treatment of a thioredoxin (TRX)-mediated diseases or disorders.

Accordingly, in one embodiment, the instant invention relates to a method of treating a thioredoxin (TRX)-mediated disease or disorder in a subject in need of treatment comprising administering to said subject a therapeutically effective amount of the hydroxamic acid derivatives described herein.

In another embodiment, the instant invention relates to the use of any one or more of the hydroxamic acid derivatives disclosed herein in the preparation of a medicament for the treatment of a thioredoxin (TRX)-mediated disease or disorder in a subject in need of such treatment.

Examples of TRX-mediated diseases include, but are not limited to, acute and chronic inflammatory diseases, autoimmune diseases, allergic diseases, diseases associated with oxidative stress, and diseases characterized by cellular hyperproliferation.

Non-limiting examples are inflammatory conditions of a joint including rheumatoid arthritis (RA) and psoriatic arthritis; inflammatory bowel diseases such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs, ischemic injury, including cerebral ischemia (e.g., brain injury as a result of trauma, epilepsy, hemorrhage or stroke, each of which may lead to neurodegeneration); HIV, heart failure, chronic, acute or malignant liver disease, autoimmune thyroiditis; systemic lupus erythematosus, Sjorgren's syndrome, lung diseases (e.g., ARDS); acute pancreatitis; amyotrophic lateral sclerosis (ALS); Alzheimer's disease; cachexia/anorexia; asthma; atherosclerosis; chronic fatigue syndrome, fever; diabetes (e.g., insulin diabetes or juvenile onset diabetes); glomerulonephritis; graft versus host rejection (e.g., in transplantation); hemohorragic shock; hyperalgesia: inflammatory bowel disease; multiple sclerosis; myopathies (e.g., muscle protein metabolism, esp. in sepsis); osteoporosis; Parkinson's disease; pain; pre-term labor; psoriasis; reperfusion injury; cytokine-induced toxicity (e.g., septic shock, endotoxic shock); side effects from radiation therapy, temporal mandibular joint disease, tumor metastasis; or an inflammatory condition resulting from strain, sprain, cartilage damage, trauma such as burn, orthopedic surgery, infection or other disease processes. Allergic diseases and conditions, include but are not limited to respiratory allergic diseases such as asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies, and the like.

As demonstrated herein, the hydroxamic acid derivatives of the present invention are useful for the treatment of diseases of the central nervous system (CNS).

Accordingly, in one embodiment, the instant invention relates to a method of treating a disease of the central nervous system (CNS) in a subject in need of treatment comprising administering to said subject a therapeutically effective amount of the hydroxamic acid derivatives described herein.

In another embodiment, the instant invention relates to the use of any one or more of the hydroxamic acid derivatives disclosed herein in the preparation of a medicament for the treatment of a disease of the central nervous system (CNS) in a subject in need of such treatment.

In a particular embodiment, the CNS disease is a neurodegenerative disease. In a further embodiment, the neurodegenerative disease is an inherited neurodegenerative disease, such as those inherited neurodegenerative diseases that are polyglutamine expansion diseases. Generally, neurodegenerative diseases can be grouped as follows:

I. Disorders characterized by progressive dementia in the absence of other prominent neurologic signs, such as Alzheimer's disease; Senile dementia of the Alzheimer type; and Pick's disease (lobar atrophy).

II. Syndromes combining progressive dementia with other prominent neurologic abnormalities such as A) syndromes appearing mainly in adults (e.g., Huntington's disease, Multiple system atrophy combining dementia with ataxia and/or manifestations of Parkinson's disease, Progressive supranuclear palsy (Steel-Richardson-Olszewski), diffuse Lewy body disease, and corticodentatonigral degeneration); and B) syndromes appearing mainly in children or young adults (e.g., Hallervorden-Spatz disease and progressive familial myoclonic epilepsy).

III. Syndromes of gradually developing abnormalities of posture and movement such as paralysis agitans (Parkinson's disease), striatonigral degeneration, progressive supranuclear palsy, torsion dystonia (torsion spasm; dystonia musculorum deformans), spasmodic torticollis and other dyskinesis, familial tremor, and Gilles de la Tourette syndrome.

IV. Syndromes of progressive ataxia such as cerebellar degenerations (e.g., cerebellar cortical degeneration and olivopontocerebellar atrophy (OPCA)); and spinocerebellar degeneration (Friedreich's atazia and related disorders).

V. Syndrome of central autonomic nervous system failure (Shy-Drager syndrome).

VI. Syndromes of muscular weakness and wasting without sensory changes (motorneuron disease such as amyotrophic lateral sclerosis, spinal muscular atrophy (e.g., infantile spinal muscular atrophy (Werdnig-Hoffman), juvenile spinal muscular atrophy (Wohlfart-Kugelberg- Welander) and other forms of familial spinal muscular atrophy), primary lateral sclerosis, and hereditary spastic paraplegia.

VII. Syndromes combining muscular weakness and wasting with sensory changes (progressive neural muscular atrophy; chronic familial polyneuropathies) such as peroneal muscular atrophy (Charcot-Marie-Tooth), hypertrophic interstitial polyneuropathy (Dejerine-Sottas), and miscellaneous forms of chronic progressive neuropathy.

VIII. Syndromes of progressive visual loss such as pigmentary degeneration of the retina (retinitis pigmentosa), and hereditary optic atrophy (Leber's disease).

The compounds of the present invention are also useful in the inhibition of smooth muscle cell proliferation and/or migration and are thus useful in the prevention and/or treatment of restenosis, for example after angioplasty and/or stent implantation.

In one embodiment, smooth muscle cell proliferation and/or migration is inhibited and restenosis is prevented and/or treated by providing a stent device having one or more of the compounds of the instant invention in or on the stent device, e.g. coated onto the stent device. The stent device is designed to controllably release the compounds of the invention, thereby inhibiting smooth muscle cell proliferation and/or migration and preventing and/or treating restenosis.

Stenosis and restenosis are conditions associated with a narrowing of blood vessels. Stenosis of blood vessels generally occurs gradually over time. Restenosis, in contrast, relates to a narrowing of blood vessels following an endovascular procedure, such as balloon angioplasty and/or stent implantation, or a vascular injury.

Balloon angioplasty is typically performed to open a stenotic blood vessel; stenting is usually performed to maintain the patency of a blood vessel after, or in combination with, balloon angioplasty. A stenotic blood vessel is opened with balloon angioplasty by navigating a balloon-tipped catheter to the site of stenosis, and expanding the balloon tip effectively to dilate the occluded blood vessel. In an effort to maintain the patency of the dilated blood vessel, a stent may be implanted in the blood vessel to provide intravascular support to the opened section of the blood vessel, thereby limiting the extent to which the blood vessel will return to its occluded state after release of the balloon catheter. Restenosis is typically caused by trauma inflicted during angioplasty, effected by, for example, balloon dilation, atherectomy or laser ablation treatment of the artery. For these procedures, restenosis occurs at a rate of about 30% to about 60% depending on the vessel location, lesion length and a number of other variables. This reduces the overall success of the relatively non-invasive balloon angioplasty and stenting procedures.

Restenosis is attributed to many factors, including proliferation of smooth muscle cells (SMC). SMC proliferation is triggered by the initial mechanical injury to the intima that is sustained at the time of balloon angioplasty and stent implantation. The process is characterized by early platelet activation and thrombus formation, followed by SMC recruitment and migration, and, finally, cellular proliferation and extracellular matrix accumulation. Damaged endothelial cells, SMCs, platelets, and macrophages secrete cytokines and growth factors which promote restenosis. SMC proliferation represents the final common pathway leading to neointimal hyperplasia. Therefore, anti-proliferative therapies aimed at inhibiting specific regulatory events in the cell cycle may constitute the most reasonable approach to restenosis after angioplasty.

The compounds of the instant invention are, as demonstrated herein, potent HDAC inhibitors that show great potential in the treatment of cell proliferative diseases or conditions. In addition, the compounds of the instant invention are potent inhibitors of SMC proliferation. Thus, the controllable release of the compounds of the invention (e.g. from a stent device), is highly advantageous in the inhibition of SMC proliferation and hence in the prevention and/or treatment of restenosis.

Thus, in one embodiment, this invention provides a stent device comprising one or more of the HDAC inhibitors of the instant invention. The stent device includes a stent body and one or more of the compounds of the invention provided on or in the stent body. In one embodiment, the compounds are included in a delivery depot which is located on or in the stent body. In another embodiment, the compounds are coated onto the stent body.

In another embodiment, this invention provides a stent device as described herein for use in inhibiting proliferation and/or migration of smooth muscle cells.

In another embodiment, this invention relates to the use of the stent device described herein for inhibiting and/or prevention restenosis in a subject in need thereof.

In another embodiment, this invention relates to the use of the compounds of the instant invention for inhibiting proliferation and/or migration of non-neoplastic smooth muscle cells in a subject.

In another embodiment, this invention relates to the use of the compounds of the instant invention for inhibiting and/or prevention restenosis in a subject in need thereof.

In another embodiment, this invention relates to a method for inhibiting proliferation and/or migration of non-neoplastic smooth muscle cells in a subject, comprising administering to the subject a compound of the present invention, in an amount effective to inhibit proliferation of smooth muscle cells in the subject.

In another embodiment, this invention relates to a method for preventing or treating restenosis after angioplasty or stent implantation in a subject, comprising administering to the subject an amount of a compound of the instant invention, effective to prevent restenosis in the subject.

In another embodiment, this invention relates to a method for preventing or treating restenosis after angioplasty or stent implantation in a subject, comprising positioning a stent device withing a lumen of a blood vessel of the subject, the stent device comprising a stent body and one or more of the compounds of the present invention provided on or in the stent body. In one embodiment, the compounds are included in a delivery depot which is located on or in the stent body. In another embodiment, the compounds are coated onto the stent body.

In yet another embodiment, the present invention provides a kit comprising a stent device as described herein, and a delivery catheter capable of positioning the stent device within a lumen of a blood vessel of a subject.

Stents are known in the art, and are typically metallic or polymeric devices that are permanently implanted in an expanded form in coronary and peripheral vessels. Stents can typically by made from a metal, such as stainless steel, tantalum, titanium alloy, cobalt alloy, silicones or a polymer such as thermoplastic elastomers including polyolefin elastomers and polyamide elastomers or any combinations thereof. A stent is typically inserted by a catheter into a vascular lumen and expanded into contact with the arterial wall, thereby providing internal support for the lumen. Examples of stents are disclosed in U.S. Pat. Nos. 4,733,665, 4,800,882 and 4,886,062.

Stents containing drug delivery systems are also known in the art. For example, U.S. Pat. Nos. 6,273,913, 6,383,215, 6,238,121, 6,231,600, 5,837,008, 5,824,048, and 5,679,400 all teach stents coated with various pharmaceutical agents. Methods of coating pharmaceutical drugs onto stents are also known to a person of skill in the art.

The term "treating" in its various grammatical forms in relation to the present invention refers to preventing (i.e., chemoprevention), curing, reversing, attenuating, alleviating, minimizing, suppressing or halting the deleterious effects of a disease state, disease progression, disease causative agent (e.g., bacteria or viruses) or other abnormal condition. For example, treatment may involve alleviating a symptom (i.e., not necessary all symptoms) of a disease or attenuating the progression of a disease. Because some of the inventive methods involve the physical removal of the etiological agent, the artisan will recognize that they are equally effective in situations where the inventive compound is administered prior to, or simultaneously with, exposure to the etiological agent (prophylactic treatment) and situations where the inventive compounds are administered after (even well after) exposure to the etiological agent.

Treatment of cancer, as used herein, refers to partially or totally inhibiting, delaying or preventing the progression of cancer including cancer metastasis; inhibiting, delaying or preventing the recurrence of cancer including cancer metastasis; or preventing the onset or development of cancer (chemoprevention) in a mammal, for example a human.

As used herein, the term "therapeutically effective amount" is intended to encompass any amount that will achieve the desired therapeutic or biological effect. The therapeutic effect is dependent upon the disease or disorder being treated or the biological effect desired. As such, the therapeutic effect can be a decrease in the severity of symptoms associated with the disease or disorder and/or inhibition (partial or complete) of progression of the disease. The amount needed to elicit the therapeutic response can be determined based on the age, health, size and sex of the subject. Optimal amounts can also be determined based on monitoring of the subject's response to treatment.

In the present invention, when the compounds are used to treat or prevent cancer, the desired biological response is partial or total inhibition, delay or prevention of the progression of cancer including cancer metastasis; inhibition, delay or prevention of the recurrence of cancer including cancer metastasis; or the prevention of the onset or development of cancer (chemoprevention) in a mammal, for example a human.

Furthermore, in the present invention, when the compounds are used to treat and/or prevent thioredoxin (TRX)-mediated diseases and conditions, a therapeutically effective amount is an amount that regulates, for example, increases, decreases or maintains a physiologically suitable level of TRX in the subject in need of treatment to elicit the desired therapeutic effect. The therapeutic effect is dependent upon the specific TRX-mediated disease or condition being treated. As such, the therapeutic effect can be a decrease in the severity of symptoms associated with the disease or disorder and/or inhibition (partial or complete) of progression of the disease or disease.

Furthermore, in the present invention, when the compounds are used to treat and/or prevent diseases or disorders of the central nervous system (CNS), a therapeutically effective amount is dependent upon the specific disease or disorder being treated. As such, the therapeutic effect can be a decrease in the severity of symptoms associated with the disease or disorder and/or inhibition (partial or complete) of progression of the disease or disorder.

In addition, a therapeutically effective amount can be an amount that inhibits histone deacetylase.

Further, a therapeutically effective amount, can be an amount that selectively induces terminal differentiation, cell growth arrest and/or apoptosis of neoplastic cells, or an amount that induces terminal differentiation of tumor cells.

The method of the instant invention is intended for the treatment or chemoprevention of human patients with cancer. However, it is also likely that the method would be effective in the treatment of cancer in other subjects. "Subject", as used herein, refers to animals such as mammals, including, but not limited to, primates (e.g., humans), cows, sheep, goats, horses, pigs, dogs, cats, rabbits, guinea pigs, rats, mice or other bovine, ovine, equine, canine, feline, rodent or murine species.

As demonstrated herein, the hydroxamic acid derivatives of the instant invention show improved activity as histone deacetylase (HDAC) inhibitors. In one embodiment, the concentration of compound required for 50% inhibition ($IC_{50}$) of histone deacetylase is below 1000 nM. In another embodiment, the concentration of compound required for 50% inhibition ($IC_{50}$) of histone deacetylase is between 500 and 1000 nM. In another embodiment, the concentration of compound required for 50% inhibition ($IC_{50}$) of histone deacetylase is between 100 and 500 nM. In another embodiment, the concentration of compound required for 50% inhibition ($IC_{50}$) of histone deacetylase is below 100 nM. In another embodiment, the concentration of compound required for 50% inhibition ($IC_{50}$) of histone deacetylase is between 10 and 100 nM. In another embodiment, the concentration of compound required for 50% inhibition ($IC_{50}$) of histone deacetylase is below 50 nM. In another embodiment, the concentration of compound required for 50% inhibition ($IC_{50}$) of histone deacetylase is between 10 and 50 nM. In another embodiment, the concentration of compound required for 50% inhibition ($IC_{50}$) of histone deacetylase is below 10 nM. In another embodiment, the concentration of compound required for 50% inhibition ($IC_{50}$) of histone deacetylase is between 1 and 10 nM. In another embodiment, the concentration of compound required for 50% inhibition ($IC_{50}$) of histone deacetylase is below 1 nM. In another embodiment, the concentration of compound required for 50% inhibition ($IC_{50}$) of histone deacetylase is between 0.1 and 1 nM.

Accordingly, in one embodiment, the invention relates to a method of inhibiting the activity of histone deacetylase comprising contacting the histone deacetylase with an effective amount of one or more of the hydroxamic acid compounds described herein.

In one embodiment, the hydroxamic acid derivatives are potent inhibitors of Class I histone deacetylases (Class I HDACs). Class I HDACs include histone deacetylase 1 (HDAC-1), histone deacetylase 2 (HDAC-2), histone deacetylase 3 (HDAC-3) and histone deacetylase 8 (HDAC-8). In a particular embodiment, the hydroxamic acid derivatives are potent inhibitors of histone deacetylase I (HDAC-1). In another embodiment, the hydroxamic acid derivatives are potent inhibitors of Class II histone deacetylases (Class II HDACs). Class II HDACs include histone deacetylase 4 (HDAC-4), histone deacetylase 5 (HDAC-8), histone deacetylase 6 (HDAC-6), histone deacetylase 7 (HDAC-7) and histone deacetylase 9 (HDAC-9).

Histone deacetylases (HDACs), as that term is used herein, are enzymes that catalyze the removal of acetyl groups from lysine residues in the amino terminal tails of the nucleosomal core histones. As such, HDACs together with histone acetyl transferases (HATs) regulate the acetylation status of histones. Histone acetylation affects gene expression and inhibitors of HDACs, such as the hydroxamic acid-based hybrid polar compound suberoylanilide hydroxamic acid (SAHA) induce growth arrest, differentiation and/or apoptosis of transformed cells in vitro and inhibit tumor growth in vivo. HDACs can be divided into three classes based on structural homology. Class I HDACs (HDACs 1, 2, 3 and 8) bear similarity to the yeast RPD3 protein, are located in the nucleus and are found in complexes associated with transcriptional co-repressors. Class II HDACs (HDACs 4, 5, 6, 7 and 9) are similar to the yeast HDA1 protein, and have both nuclear and cytoplasmic subcellular localization. Both Class I and II HDACs are inhibited by hydroxamic acid-based HDAC inhibitors, such as SAHA. Class III HDACs form a structurally distant class of NAD dependent enzymes that are related to the yeast SIR2 proteins and are not inhibited by hydroxamic acid-based HDAC inhibitors.

Histone deacetylase inhibitors or HDAC inhibitors, as that term is used herein are compounds that are capable of inhibiting the deacetylation of histones in vivo, in vitro or both. As such, HDAC inhibitors inhibit the activity of at least one histone deacetylase. As a result of inhibiting the deacetylation of at least one histone, an increase in acetylated histone occurs and accumulation of acetylated histone is a suitable biological marker for assessing the activity of HDAC inhibitors. Therefore, procedures that can assay for the accumulation of acetylated histones can be used to determine the HDAC inhibitory activity of compounds of interest. It is understood that compounds that can inhibit histone deacetylase activity can also bind to other substrates and as such can inhibit other biologically active molecules such as enzymes. It is also to be understood that the compounds of the instant invention are capable of inhibiting any of the histone deacetylases set forth above, or any other histone deacetylases.

For example, in patients receiving HDAC inhibitors, the accumulation of acetylated histones in peripheral mononuclear cells as well as in tissue treated with HDAC inhibitors can be determined against a suitable control.

HDAC inhibitory activity of a particular compound can be determined in vitro using, for example, an enzymatic assay which shows inhibition of at least one histone deacetylase. Further, determination of the accumulation of acetylated histones in cells treated with a particular composition can be determinative of the HDAC inhibitory activity of a compound.

Assays for the accumulation of acetylated histones are well known in the literature. See, for example, Marks, P. A. et al., *J. Natl. Cancer Inst.*, 92:1210-1215, 2000, Butler, L. M. et al., *Cancer Res.* 60:5165-5170 (2000), Richon, V. M. et al., *Proc. Natl. Acad. Sci., USA*, 95:3003-3007, 1998, and Yoshida, M. et al., *J. Biol. Chem.*, 265:17174-17179, 1990.

For example, an enzymatic assay to determine the activity of an HDAC inhibitor compound can be conducted as follows. Briefly, the effect of an HDAC inhibitor compound on affinity purified human epitope-tagged (Flag) HDAC1 can be assayed by incubating the enzyme preparation in the absence of substrate on ice for about 20 minutes with the indicated amount of inhibitor compound. Substrate ([$^3$H]acetyl-4-labelled murine erythroleukemia cell-derived histone) can be added and the sample can be incubated for 20 minutes at 37° C. in a total volume of 30 µL. The reaction can then be stopped and released acetate can be extracted and the amount of radioactivity release determined by scintillation counting. An alternative assay useful for determining the activity of an HDAC inhibitor compound is the "HDAC Fluorescent Activity Assay; Drug Discovery Kit-AK-500" available from BIOMOL® Research Laboratories, Inc., Plymouth Meeting, Pa.

In vivo studies can be conducted as follows. Animals, for example, mice, can be injected intraperitoneally with an HDAC inhibitor compound. Selected tissues, for example, brain, spleen, liver etc, can be isolated at predetermined times, post administration. Histones can be isolated from tissues essentially as described by Yoshida et al., J. Biol. Chem. 265:17174-17179, 1990. Equal amounts of histones (about 1 µg) can be electrophoresed on 15% SDS-polyacrylamide gels and can be transferred to Hybond-P filters (available from Amersham). Filters can be blocked with 3% milk and can be probed with a rabbit purified polyclonal anti-acetylated histone H4 antibody (αAc-H4) and anti-acetylated histone H3 antibody (αAc-H3) (Upstate Biotechnology, Inc.). Levels of acetylated histone can be visualized using a horseradish peroxidase-conjugated goat anti-rabbit antibody (1:5000) and the SuperSignal chemiluminescent substrate (Pierce). As a loading control for the histone protein, parallel gels can be run and stained with Coomassie Blue (CB).

In addition, hydroxamic acid-based HDAC inhibitors have been shown to up regulate the expression of the $p21^{WAF1}$ gene. The $p21^{WAF1}$ protein is induced within 2 hours of culture with HDAC inhibitors in a variety of transformed cells using standard methods. The induction of the $p21^{WAF1}$ gene is associated with accumulation of acetylated histones in the chromatin region of this gene. Induction of $p21^{WAF1}$ can therefore be recognized as involved in the G1 cell cycle arrest caused by HDAC inhibitors in transformed cells.

Typically, HDAC inhibitors fall into five general classes: 1) hydroxamic acid derivatives; 2) Short-Chain Fatty Acids (SCFAs); 3) cyclic tetrapeptides; 4) benzamides; and 5) electrophilic ketones. Examples of such HDAC inhibitors are set forth below.

A. Hydroxamic Acid Derivatives such as: suberoylanilide hydroxamic acid (SAHA) (Richon et al., *Proc. Natl. Acad. Sci. USA* 95, 3003-3007 (1998)); m-carboxycinnamic acid bishydroxamide (CBHA) (Richon et al., supra); pyroxamide; trichostatin analogues such as trichostatin A (TSA) and trichostatin C (Koghe et al. 1998. *Biochem. Pharmacol.* 56: 1359-1364); salicylhydroxamic acid (Andrews et al., *International J. Parasitology* 30, 761-768 (2000)); suberoyl bishydroxamic acid (SBHA) (U.S. Pat. No. 5,608, 108); azelaic bishydroxamic acid (ABHA) (Andrews et al., supra); azelaic-1-hydroxamate-9-anilide (AAHA) (Qiu et al., *Mol. Biol. Cell* 11, 2069-2083 (2000)); 6-(3-chlorophenylureido) carpoic hydroxamic acid (3Cl-UCHA); oxamflatin [(2E)-5-[3-[(phenylsulfonyl)amino]phenyl]-pent-2-en-4-ynohydroxamic acid] (Kim et al. *Oncogene*, 18: 2461 2470 (1999)); A-161906, Scriptaid (Su et al. 2000 *Cancer Research*, 60: 3137-3142); PXD-101 (Prolifix); LAQ-824; CHAP; MW2796 (Andrews et al., supra); MW2996 (Andrews et al., supra); or any of the hydroxamic acids disclosed in U.S. Pat. Nos. 5,369,108, 5,932,616, 5,700,811, 6,087,367 and 6,511,990.

B. Cyclic Tetrapeptides such as: trapoxin A (TPX)-cyclic tetrapeptide (cyclo-(L-phenylalanyl-L-phenylalanyl-D-pipecolinyl-L-2-amino-8-oxo-9,10-epoxy decanoyl)) (Kijima et al., *J Biol. Chem.* 268, 22429-22435 (1993)); FR901228 (FK 228, depsipeptide) (Nakajima et al., *Ex. Cell Res.* 241, 126-133 (1998)); FR225497 cyclic tetrapeptide (H. Mori et al., PCT Application WO 00/08048 (17 Feb. 2000)); apicidin cyclic tetrapeptide [cyclo(N—O-methyl-L-tryptophanyl-L-isoleucinyl-D-pipecolinyl-L-2-amino-8-oxodecanoyl)] (Darkin-Rattray et al., *Proc. Natl. Acad. Sci. USA* 93,1314313147 (1996)); apicidin Ia, apicidin Ib, apicidin Ic, apicidin IIa, and apicidin IIb (P. Dulski et al., PCT Application WO 97/11366); CHAP, HC-toxin cyclic tetrapeptide (Bosch et al., *Plant Cell* 7, 1941-1950

(1995)); WF27082 cyclic tetrapeptide (PCT Application WO 98/48825); and chlamydocin (Bosch et al., supra).

C. Short Chain Fatty Acid (SCFA) Derivatives such as: sodium butyrate (Cousens et al., *J. Biol. Chem.* 254, 1716-1723 (1979)); isovalerate (McBain et al., *Biochem. Pharm.* 53: 1357-1368 (1997)); valerate (McBain et al., supra); 4-phenylbutyrate (4-PBA) (Lea and Tulsyan, *Anticancer Research*, 15, 879-873 (1995)); phenylbutyrate (PB) (Wang et al., *Cancer Research*, 59, 2766-2799 (1999)); propionate (McBain et al., supra); butyramide (Lea and Tulsyan, supra); isobutyramide (Lea and Tulsyan, supra); phenylacetate (Lea and Tulsyan, supra); 3-bromopropionate (Lea and Tulsyan, supra); tributyrin (Guan et al., *Cancer Research*, 60, 749-755 (2000)); valproic acid, valproate and Pivanex™.

D. Benzamide Derivatives such as: CI-994; MS-275 [N-(2-aminophenyl)-4-[N-(pyridin-3-yl methoxycarbonyl)aminomethyl]benzamide] (Saito et al., *Proc. Natl. Acad. Sci. USA* 96, 4592-4597 (1999)); and 3'-amino derivative of MS-275 (Saito et al., supra).

E. Electrophilic Ketone Derivatives such as: trifluoromethyl ketones (Frey et al, *Bioorganic & Med. Chem. Lett.* (2002), 12, 3443-3447; U.S. Pat. No. 6,511,990) and α-keto amides such as N-methyl-α-ketoamides F. Other HDAC Inhibitors such as: natural products, psammaplins and Depudecin (Kwon et al. 1998. *PNAS* 95: 3356-3361).

The hydroxamic acid compounds of the instant invention can be administered alone or in combination with other therapies suitable for the disease or disorder being treated. Where separate dosage formulations are used, the hydroxamic acid compound and the other therapeutic agent can be administered at essentially the same time (concurrently) or at separately staggered times (sequentially). The pharmaceutical combination is understood to include all these regimens. Administration in these various ways are suitable for the present invention as long as the beneficial therapeutic effect of the hydroxamic acid compound and the other therapeutic agent are realized by the patient at substantially the same time. Such beneficial effect is preferably achieved when the target blood level concentrations of each active drug are maintained at substantially the same time.

A person of skill in the art would be able to discern which combinations of agents would be useful based on the disease being treated, e.g. which cancer, which neurodegenerative disease or which inflammatory disease is involved.

The hydroxamic acid derivatives can be administered in combination with any one or more of an HDAC inhibitor (e.g. any one or more of the HDAC inhibitors described above), an alkylating agent, an antibiotic agent, an antimetabolic agent, a hormonal agent, a plant-derived agent, a biologic agent, a gene therapy agent, an anti-angiogenic agent, a differentiation inducing agent, a retinoid receptor modulator, a cytotoxic/cytostatic agent, an anti-proliferative agent, an HMG-CoA reductase inhibitor, a prenyl-protein transferase inhibitor, an agent that interferes with cell cycle checkpoints, an inhibitor of cell proliferation and survival signaling, an apoptosis inducing agent, a cell growth arrest inducing agent, or any combination thereof. In addition, the instant compounds are particularly useful when co-administered with radiation therapy.

"Alkylating agents" react with nucleophilic residues, such as the chemical entities on the nucleotide precursors for DNA production. They affect the process of cell division by alkylating these nucleotides and preventing their assembly into DNA.

Examples of alkylating agents include, but are not limited to, bischloroethylamines (nitrogen mustards, e.g., chlorambucil, cyclophosphamide, ifosfamide, mechlorethamine, melphalan, uracil mustard), aziridines (e.g., thiotepa), alkyl alkone sulfonates (e.g., busulfan), nitrosoureas (e.g., carmustine, lomustine, streptozocin), nonclassic alkylating agents (altretamine, dacarbazine, and procarbazine), platinum compounds (carboplatin and cisplatin). These compounds react with phosphate, amino, hydroxyl, sulfhydryl, carboxyl, and imidazole groups.

Under physiological conditions, these drugs ionize and produce positively charged ion that attach to susceptible nucleic acids and proteins, leading to cell cycle arrest and/or cell death. The alkylating agents are cell cycle phase nonspecific agents because they exert their activity independently of the specific phase of the cell cycle. The nitrogen mustards and alkyl alkone sulfonates are most effective against cells in the $G_1$ or M phase. Nitrosoureas, nitrogen mustards, and aziridines impair progression from the $G_1$ and S phases to the M phases. Chabner and Collins eds. (1990) "Cancer Chemotherapy: Principles and Practice", Philadelphia: JB Lippincott.

The alkylating agents are active against wide variety of neoplastic diseases, with significant activity in the treatment of leukemias and lymphomas as well as solid tumors. Clinically this group of drugs is routinely used in the treatment of acute and chronic leukemias; Hodgkin's disease; non-Hodgkin's lymphoma; multiple myeloma; primary brain tumors; carcinomas of the breast, ovaries, testes, lungs, bladder, cervix, head and neck, and malignant melanoma.

"Antibiotic agents" (e.g., cytotoxic antibiotics) act by directly inhibiting DNA or RNA synthesis and are effective throughout the cell cycle. Examples of antibiotic agents include anthracyclines (e.g., doxorubicin, daunorubicin, epirubicin, idarubicin and anthracenedione), mitomycin C, bleomycin, dactinomycin, and plicatomycin. These antibiotic agents interfere with cell growth by targeting different cellular components. For example, anthracyclines are generally believed to interfere with the action of DNA topoisomerase II in the regions of transcriptionally active DNA, which leads to DNA strand scissions.

Bleomycin is generally believed to chelate iron and forms an activated complex, which then binds to bases of DNA, causing strand scissions and cell death.

The antibiotic agents have been used as therapeutics across a range of neoplastic diseases, including carcinomas of the breast, lung, stomach and thyroids, lymphomas, myelogenous leukemias, myelomas, and sarcomas.

"Antimetabolic agents" (i.e., antimetabolites) are a group of drugs that interfere with metabolic processes vital to the physiology and proliferation of cancer cells. Actively proliferating cancer cells require continuous synthesis of large quantities of nucleic acids, proteins, lipids, and other vital cellular constituents.

Many of the antimetabolites inhibit the synthesis of purine or pyrimidine nucleosides or inhibit the enzymes of DNA replication. Some antimetabolites also interfere with the synthesis of ribonucleosides and RNA and/or amino acid metabolism and protein synthesis as well. By interfering with the synthesis of vital cellular constituents, antimetabolites can delay or arrest the growth of cancer cells. Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine.

Antimetabolic agents have widely used to treat several common forms of cancer including carcinomas of colon, rectum, breast, liver, stomach and pancreas, malignant melanoma, acute and chronic leukemia and hair cell leukemia.

"Hormonal agents" are a group of drugs that regulate the growth and development of their target organs. Some of the hormonal agents are sex steroids and their derivatives and analogs thereof, such as estrogens, progestogens, anti-estrogens, androgens, anti-androgens and progestins. Other hormonal agents are small molecules that regulate their target receptors. These hormonal agents may serve as antagonists of receptors for the sex steroids to down regulate receptor expression and transcription of vital genes. Examples of such hormonal agents are synthetic estrogens (e.g., diethylstibestrol), estrogen receptor modulators, selective estrogen receptor modulators (SERMs), antiestrogens (e.g., tamoxifen, toremifene, fluoxymesterol and raloxifene), androgen receptor modulators, selective androgen receptor modulators (SARM), antiandrogens (e.g. bicalutamide, nilutamide, flutamide), aromatase inhibitors (e.g., aminoglutethimide, anastrozole and tetrazole), luteinizing hormone release hormone (LHRH) analogues, ketoconazole, goserelin acetate, leuprolide, megestrol acetate and mifepristone.

Hormonal agents are used to treat breast cancer, prostate cancer, melanoma and meningioma. Because the major action of hormones is mediated through steroid receptors, 60% receptor-positive breast cancer responded to first-line hormonal therapy; and less than 10% of receptor-negative tumors responded. Specifically, progestogens are used to treat endometrial cancers, since these cancers occur in women that are exposed to high levels of oestrogen unopposed by progestogen. Antiandrogens are used primarily for the treatment of prostate cancer, which is hormone dependent. They are used to decrease levels of testosterone, and thereby inhibit growth of the tumor.

Hormonal treatment of breast cancer involves reducing the level of oestrogen-dependent activation of oestrogen receptors in neoplastic breast cells. Anti-oestrogens act by binding to oestrogen receptors and prevent the recruitment of coactivators, thus inhibiting the oestrogen signal.

LHRH analogues are used in the treatment of prostate cancer to decrease levels of testosterone and so decrease the growth of the tumor.

Aromatase inhibitors act by inhibiting the enzyme required for hormone synthesis. In post-menopausal women, the main source of oestrogen is through the conversion of androstenedione by aromatase.

Estrogen receptor modulators refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

Androgen receptor modulators refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Plant-derived agents" are a group of drugs that are derived from plants or modified based on the molecular structure of the agents. They inhibit cell replication by preventing the assembly of the cell's components that are essential to cell division.

Examples of plant derived agents include vinca alkaloids (e.g., vincristine, vinblastine, vindesine, vinzolidine and vinorelbine), podophyllotoxins (e.g., etoposide (VP-16) and teniposide (VM-26)), taxanes (e.g., paclitaxel and docetaxel). These plant-derived agents generally act as antimitotic agents that bind to tubulin and inhibit mitosis. Podophyllotoxins such as etoposide are believed to interfere with DNA synthesis by interacting with topoisomerase II, leading to DNA strand scission.

Plant-derived agents are used to treat many forms of cancer. For example, vincristine is used in the treatment of the leukemias, Hodgkin's and non-Hodgkin's lymphoma, and the childhood tumors neuroblastoma, rhabdomyosarcoma, and Wilm's tumor. Vinblastine is used against the lymphomas, testicular cancer, renal cell carcinoma, mycosis fungoides, and Kaposi's sarcoma. Doxetaxel has shown promising activity against advanced breast cancer, non-small cell lung cancer (NSCLC), and ovarian cancer.

Etoposide is active against a wide range of neoplasms, of which small cell lung cancer, testicular cancer, and NSCLC are most responsive.

"Biologic agents" are a group of biomolecules that elicit cancer/tumor regression when used alone or in combination with chemotherapy and/or radiotherapy. Examples of biologic agents include immuno-modulating proteins such as cytokines, monoclonal antibodies against tumor antigens, tumor suppressor genes, and cancer vaccines.

Cytokines possess profound immunomodulatory activity. Some cytokines such as interleukin-2 (IL-2, aldesleukin) and interferon-α (IFN-α) demonstrated antitumor activity and have been approved for the treatment of patients with metastatic renal cell carcinoma and metastatic malignant melanoma. IL-2 is a T-cell growth factor that is central to T-cell-mediated immune responses. The selective antitumor effects of IL-2 on some patients are believed to be the result of a cell-mediated immune response that discriminate between self and nonself.

Interferon-α includes more than 23 related subtypes with overlapping activities. IFN-a has demonstrated activity against many solid and hematologic malignancies, the later appearing to be particularly sensitive.

Examples of interferons include, interferon-α, interferon-β (fibroblast interferon) and interferon-γ (fibroblast interferon). Examples of other cytokines include erythropoietin (epoietin-α), granulocyte-CSF (filgrastin), and granulocyte, macrophage-CSF (sargramostim). Other immuno-modulating agents other than cytokines include bacillus Calmette-Guerin, levamisole, and octreotide, a long-acting octapeptide that mimics the effects of the naturally occurring hormone somatostatin.

Furthermore, the anti-cancer treatment can comprise treatment by immunotherapy with antibodies and reagents used in tumor vaccination approaches. The primary drugs in this therapy class are antibodies, alone or carrying compounds such as toxins or chemotherapeutics/cytotoxics to cancer cells. Monoclonal antibodies against tumor antigens are antibodies elicited against antigens expressed by tumors, preferably tumor-specific antigens. For example, monoclonal antibody HERCEPTIN® (trastuzumab) is raised against human epidermal growth factor receptor2 (HER2) that is overexpressed in some breast tumors including metastatic breast cancer. Overexpression of HER2 protein is associated with more aggressive disease and poorer prognosis in the clinic.

HERCEPTIN® is used as a single agent for the treatment of patients with metastatic breast cancer whose tumors over express the HER2 protein.

Another example of monoclonal antibodies against tumor antigens is RITUXAN® (rituximab) that is raised against CD20 on lymphoma cells and selectively deplete normal and malignant CD20+pre-B and mature B cells.

RITUXAN is used as single agent for the treatment of patients with relapsed or refractory low-grade or follicular, CD20+, B cell non-Hodgkin's lymphoma. MYELOTARG® (gemtuzumab ozogamicin) and CAMPATH® (alemtuzumab) are further examples of monoclonal antibodies against tumor antigens that may be used.

In addition, examples of monoclonal antibody targeted therapeutic agents include those therapeutic agents which have cytotoxic agents or radioisotopes attached to a cancer cell specific or target cell specific monoclonal antibody. Examples include Bexxar.

Tumor suppressor genes are genes that function to inhibit the cell growth and division cycles, thus preventing the development of neoplasia. Mutations in tumor suppressor genes cause the cell to ignore one or more of the components of the network of inhibitory signals, overcoming the cell cycle checkpoints and resulting in a higher rate of controlled cell growth-cancer. Examples of the tumor suppressor genes include Duc-4, NF-1, NF-2, RB, p53, WT1, BRCA1 and BRCA2.

DPC4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. P53 codes for p53 protein that regulates cell division and can induce apoptosis. Mutation and/or inaction of p53 is found in a wide ranges of cancers. WTI is involved in Wilm's tumor of the kidneys. BRCA1 is involved in breast and ovarian cancer, and BRCA2 is involved in breast cancer. The tumor suppressor gene can be transferred into the tumor cells where it exerts its tumor suppressing functions.

Cancer vaccines are a group of agents that induce the body's specific immune response to tumors. Most of cancer vaccines under research and development and clinical trials are tumor-associated antigens (TAAs). TAAs are structures (i.e., proteins, enzymes or carbohydrates) that are present on tumor cells and relatively absent or diminished on normal cells. By virtue of being fairly unique to the tumor cell, TAAs provide targets for the immune system to recognize and cause their destruction. Examples of TAAs include gangliosides (GM2), prostate specific antigen (PSA), α-fetoprotein (AFP), carcinoembryonic antigen (CEA) (produced by colon cancers and other adenocarcinomas, e.g., breast, lung, gastric, and pancreatic cancers), melanoma-associated antigens (MART-1, gap100, MAGE 1,3 tyrosinase), papillomavirus E6 and E7 fragments, whole cells or portions/lysates of autologous tumor cells and allogeneic tumor cells.

Recent developments have introduced, in addition to the traditional cytotoxic and hormonal therapies used to treat cancer, additional therapies for the treatment of cancer. For example, many forms of gene therapy are undergoing preclinical or clinical trials. Thus, another embodiment of the instant invention is the use of the presently disclosed compounds in combination with gene therapy for the treatment of cancer. For an overview of genetic strategies to treating cancer see Hall et al (*Am J Hum Genet.* 61:785-789, 1997) and Kufe et al (*Cancer Medicine,* 5th Ed, pp 876-889, B C Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069, 134, for example), a uPA/uPAR antagonist ("Adenovirus-Mediated Delivery of a uPA/uPAR Antagonist Suppresses Angiogenesis-Dependent Tumor Growth and Dissemination in Mice," *Gene Therapy,* August 1998; 5(8): 1105-13), and interferon gamma (*J Immunol* 2000; 164:217-222).

In addition, approaches are currently under development, that are based on the inhibition of tumor vascularization (angiogenesis). The aim of this concept is to cut off the tumor from nutrition and oxygen supply provided by a newly built tumor vascular system. "Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (*PNAS,* Vol. 89, p. 7384 (1992); *JNCI,* Vol. 69, p. 475 (1982); *Arch. Opthalnol.,* Vol. 108, p. 573 (1990); *Anat. Rec.,* Vol. 238, p. 68 (1994); *FEBS Letters,* Vol. 372, p. 83 (1995); *Clin, Orthop.* Vol. 313, p. 76 (1995); *J. Mol. Endocrinol.,* Vol. 16, p. 107 (1996); *Jpn. J. Pharmacol.,* Vol. 75, p. 105 (1997); *Cancer Res.,* Vol. 57, p. 1625 (1997); *Cell,* Vol. 93, p. 705 (1998); *Intl. J. Mol. Med.,* Vol. 2, p. 715 (1998); *J. Biol. Chem.,* Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology,* Vol. 17, pp. 963-968 (October 1999); Kim et al., *Nature,* 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see Thrombosis Res. 101:329-354 (2001)). TAFIa inhibitors have been described in PCT Publication WO 03/013,526 and U.S. Ser. No. 60/349,925 (filed Jan. 18, 2002).

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

In addition, cancer therapy is also being attempted by the induction of terminal differentiation of the neoplastic cells. Suitable differentiation agents include the compounds disclosed in any one or more of the following references, the contents of which are incorporated by reference herein.

a) Polar compounds (Marks et al (1987); , Friend, C., Scher, W., Holland, J. W., and Sato, T. (1971) *Proc. Natl. Acad. Sci.* (USA) 68: 378-382; Tanaka, M., Levy, J., Terada, M., Breslow, R., Rifkind, R. A., and Marks, P. A. (1975) *Proc. Natl. Acad. Sci.* (USA) 72: 1003-1006; Reuben, R. C., Wife, R. L., Breslow, R., Rifkind, R. A., and Marks, P. A. (1976) *Proc. Natl. Acad. Sci.* (USA) 73: 862-866);

b) Derivatives of vitamin D and retinoic acid (Abe, E., Miyaura, C., Sakagami, H., Takeda, M., Konno, K., Yamazaki, T., Yoshika, S., and Suda, T. (1981) *Proc. Natl. Acad. Sci.* (USA) 78: 4990-4994; Schwartz, E. L., Snoddy, J. R., Kreutter, D., Rasmussen, H., and Sartorelli, A. C. (1983) *Proc. Am. Assoc. Cancer Res.* 24: 18; Tanenaga, K., Hozumi, M., and Sakagami, Y. (1980) *Cancer Res.* 40: 914-919);

c) Steroid hormones (Lotem, J. and Sachs, L. (1975) *Int. J. Cancer* 15: 731-740);

d) Growth factors (Sachs, L. (1978) *Nature* (Lond.) 274: 535, Metcalf, D. (1985) *Science,* 229: 16-22);

e) Proteases (Scher, W., Scher, B. M., and Waxman, S. (1983) *Exp. Hematol.* 11: 490-498; Scher, W., Scher, B. M., and Waxman, S. (1982) *Biochem. & Biophys. Res. Comm.* 109: 348-354);

f) Tumor promoters (Huberman, E. and Callaham, M. F. (1979) *Proc. Natl. Acad. Sci.* (USA) 76: 1293-1297; Lottem, J. and Sachs, L. (1979) *Proc. Natl. Acad. Sci.* (USA) 76: 5158-5162); and g) inhibitors of DNA or RNA synthesis (Schwartz, E. L. and Sartorelli, A. C. (1982) *Cancer Res.* 42: 2651-2655, Terada, M., Epner, E., Nudel, U., Salmon, J., Fibach, E., Rifkind, R. A., and Marks, P. A. (1978) *Proc. Natl. Acad. Sci.* (USA) 75: 2795-2799; Morin, M. J. and Sartorelli, A. C. (1984) *Cancer Res.* 44: 2807-2812; Schwartz, E. L., Brown, B. J., Nierenberg, M., Marsh, J. C., and Sartorelli, A. C. (1983) *Cancer Res.* 43: 2725-2730; Sugano, H., Furusawa, M., Kawaguchi, T., and Ikawa, Y. (1973) *Bibl. Hematol.* 39: 943-954; Ebert, P. S., Wars, I., and Buell, D. N. (1976) *Cancer Res.* 36: 1809-1813; Hayashi, M., Okabe, J., and Hozumi, M. (1979) Gann 70: 235-238).

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents (such as those described above), tumor necrosis factors, intercalators, hypoxia activatable compounds, microtubule inhibitors/microtubule-stabilizing agents, inhibitors of mitotic kinesins, inhibitors of kinases involved in mitotic progression, haematopoietic growth factors, topoisomerase inhibitors, biological response modifiers, proteasome inhibitors and ubiquitin ligase inhibitors. In addition, cyclotoxic/cytostatic agents include any of the antimetabolites; hormonal/anti-hormonal therapeutic agents, and monoclonal antibody targeted therapeutic agents described above.

Examples of cytotoxic agents include, but are not limited to, sertenef, cachectin, ifosfamide, tasonermin, lonidamine, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans,trans,trans)-bis-mu-(hexane-1,6-diamine)-mu-[diamine-platinum II]bis[diamine(chloro)platinum II]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin (see WO 00/50032).

An example of a hypoxia activatable compound is tirapazamine.

Examples of proteasome inhibitors include but are not limited to lactacystin and bortezomib.

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydrooxy-3,5-dimethoxyphenyl]-5,5a,6,8,8a,9-hexahydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in PCT Publications WO 01/30768, WO 01/98278, WO 03/050,064, WO 03/050,122, WO 03/049,527, WO 03/049,679, WO 03/049,678 and WO 03/39460 and pending PCT Appl. Nos. US03/06403 (filed Mar. 4, 2003), US03/15861 (filed May 19, 2003), US03/15810 (filed May 19, 2003), US03/18482 (filed Jun. 12, 2003) and US03/18694 (filed Jun. 12, 2003). In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

"inhibitors of kinases involved in mitotic progression" include, but are not limited to, inhibitors of aurora kinase, inhibitors of Polo-like kinases (PLK) (in particular inhibitors of PLK-1), inhibitors of bub-1 and inhibitors of bub-R1.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,1'-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896) and atorvastatin (LIPITOR®; see U.S. Pat. Nos. 5,273, 995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt having inhibitory activity, and therefore the use of such salts, esters, open-acid and lactone forms inc luster forms of compounds which have HMG-CoA reductase are within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359.

For an example of the role of a prenyl-protein transferase inhibitor on angiogenesis see European J. of Cancer, Vol. 35, No. 9, pp. 1394-1401 (1999).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Inhibitors of cell proliferation and survival signaling pathway" refer to pharmaceutical agents that inhibit cell surface receptors and signal transduction cascades downstream of those surface receptors. Such agents include inhibitors of EGFR (for example gefitinib and erlotinib), inhibitors of ERB-2 (for example trastuzumab), inhibitors of IGFR, inhibitors of cytokine receptors, inhibitors of MET, inhibitors of PI3K (for example LY294002), serine/threonine kinases (including but not limited to inhibitors of Akt such as described in WO 02/083064, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779). Such agents include small molecule inhibitor compounds and antibody antagonists.

"Apoptosis inducing agents" include activators of TNF receptor family members (including the TRAIL receptors).

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of IC50 for COX-2 over IC50 for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550, 142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633, 272, and U.S. Pat. No. 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine;

or a pharmaceutically acceptable salt thereof.

Compounds that have been described as specific inhibitors of COX-2 and are therefore useful in the present invention include, but are not limited to: parecoxib, CELEBREX® and BEXTRA® or a pharmaceutically acceptable salt thereof.

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl]indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Opthalmol. Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119: 709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. Nos. 60/235,708 and 60/244,697).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the instant invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the instant invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the instant compounds.

Neurokinin-1 receptor antagonists of use in conjunction with the compounds of the instant invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92122569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the instant invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

Thus, the scope of the instant invention encompasses the use of the instantly claimed compounds in combination with a second compound selected from: HDAC inhibitor (e.g. any one or more of the HDAC inhibitors described above), an alkylating agent, an antibiotic agent, an antimetabolic agent, a hormonal agent, a plant-derived agent, a biologic agent, a gene therapy agent, an anti-angiogenic agent, a differentiation inducing agent, a retinoid receptor modulator, a cytotoxic/cytostatic agent, an anti-proliferative agent, an HMG-CoA reductase inhibitor, a prenyl-protein transferase inhibitor, an agent that interferes with cell cycle checkpoints, an inhibitor of cell proliferation and survival signaling, an apoptosis inducing agent, a cell growth arrest inducing agent, a bisphosphonate, or any combination thereof.

Also included in the scope of the claims is a method of treating cancer that comprises administering a therapeutically effective amount of a compound of Formula I in combination with radiation therapy and/or in combination with a compound selected from: an alkylating agent, an antibiotic agent, an antimetabolic agent, a hormonal agent, a plant-derived agent, a biologic agent, a gene therapy agent, an anti-angiogenic agent, a differentiation inducing agent, a retinoid receptor modulator, a cytotoxic/cytostatic agent, an anti-proliferative agent, an HMG-CoA reductase inhibitor, a prenyl-protein transferase inhibitor, an agent that interferes with cell cycle checkpoints, an inhibitor of cell proliferation and survival signaling, an apoptosis inducing agent, a cell growth arrest inducing agent, a bisphosphonate, or any combination thereof.

The instant invention also includes a pharmaceutical composition useful for treating or preventing cancer that comprises a therapeutically effective amount of a compound of Formula I and a compound selected from: an alkylating agent, an antibiotic agent, an antimetabolic agent, a hormonal agent, a plant-derived agent, a biologic agent, a gene therapy agent, an anti-angiogenic agent, a differentiation inducing agent, a retinoid receptor modulator, a cytotoxic/cytostatic agent, an anti-proliferative agent, an HMG-CoA reductase inhibitor, a prenyl-protein transferase inhibitor, an agent that interferes with cell cycle checkpoints, an inhibitor of cell proliferation and survival signaling, an apoptosis inducing agent, a cell growth arrest inducing agent, a bisphosphonate, or any combination thereof.

The dosage regimen utilizing the hydroxamic acid derivatives of the present invention can be selected in accordance with a variety of factors including type, species, age, weight, sex and the type of cancer being treated; the severity (i.e., stage) of the disease to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease.

For oral administration, suitable daily dosages are for example between about 5-4000 mg/m$^2$ administered orally once-daily, twice-daily or three times-daily, continuous (every day) or intermittently (e.g., 3-5 days a week). For example, when used to treat the desired disease, the dose of the hydroxamic acid can range between about 2 mg to about 2000 mg per day.

The hydroxamic acid derivative is administered once daily (QD), or divided into multiple daily doses such as twice daily (BID), and three times daily (TID). For administration once a day, a suitably prepared medicament would therefore contain all of the needed daily dose. For administration twice a day, a suitably prepared medicament would therefore contain half of the needed daily dose. For administration three times a day, a suitably prepared medicament would therefore contain one third of the needed daily dose.

In addition, the administration can be continuous, i.e., every day, or intermittently. The terms "intermittent" or "intermittently" as used herein means stopping and starting at either regular or irregular intervals. For example, intermittent administration of an HDAC inhibitor may be administration one to six days per week or it may mean administration in cycles (e.g., daily administration for two to eight consecutive weeks, then a rest period with no administration for up to one week) or it may mean administration on alternate days.

Typically, an intravenous formulation may be prepared which contains a concentration of the hydroxamic acid derivative of between about 1.0 mg/mL to about 10 mg/mL. In one example, a sufficient volume of intravenous formulation can be administered to a patient in a day such that the total dose for the day is between about 10 and about 1500 mg/m$^2$.

Subcutaneous formulations, preferably prepared according to procedures well known in the art at a pH in the range between about 5 and about 12, also include suitable buffers and isotonicity agents, as described below. They can be formulated to deliver a daily dose of HDAC inhibitor in one or more daily subcutaneous administrations, e.g., one, two or three times each day.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regime. It should be apparent to a person skilled in the art that the various modes of administration described herein merely set forth specific embodiments and should not be construed as limiting the broad scope of the invention.

The compounds of this invention may be administered to mammals, preferably humans, either alone or, preferably, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

In another aspect of the invention, the compounds of this invention may be administered to mammals, preferably humans, by administering to the mammal, either alone or, in combination with pharmaceutically acceptable carriers, excipients or diluents, in a pharmaceutical composition, the metabolic precursor compound of the compound of the instant invention. Such a metabolic precursor compound is described in U.S. Patent Appl. Nos. 60/388,621, 60/403,830, and 60/426,940. Compositions comprising such metabolic precursor compounds, which are also inhibitors of KSP, are also described in those U.S. patent applications.

As used herein, the term "composition" is intended to encompass a product comprising the specified ingredients in the specific amounts, as well as any product which results, directly or indirectly, from combination of the specific ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the instant invention may also be delivered as a suppository employing bases such as cocoa butter, glycerinated gelatin, hydrogenated vegetable oils, mixtures of polyethylene glycols of various molecular weights and fatty acid esters of polyethylene glycol.

The present invention also provides methods of using the hydroxamic acid derivatives of the instant invention for inducing terminal differentiation, cell growth arrest and/or apoptosis of neoplastic cells thereby inhibiting the proliferation of such cells. The methods can be practiced in vivo or in vitro.

In one embodiment, the present invention provides in vitro methods for selectively inducing terminal differentiation, cell growth arrest and/or apoptosis of neoplastic cells, thereby inhibiting proliferation of such cells, by contacting the cells with an effective amount of any one or more of the hydroxamic acid derivatives described herein.

In a particular embodiment, the present invention relates to an in vitro method of selectively inducing terminal differentiation of neoplastic cells and thereby inhibiting proliferation of such cells. The method comprises contacting the cells under suitable conditions with an effective amount of one or more of the hydroxamic acid compounds described herein.

In another embodiment, the invention relates to an in vitro method of selectively inducing cell growth arrest of neoplastic cells and thereby inhibiting proliferation of such cells. The method comprises contacting the cells under suitable conditions with an effective amount of one or more of the hydroxamic acid compounds described herein.

In another embodiment, the invention relates to an in vitro method of selectively inducing apoptosis of neoplastic cells and thereby inhibiting proliferation of such cells. The method comprises contacting the cells under suitable conditions with an effective amount of one or more of the hydroxamic acid compounds described herein.

In another embodiment, the invention relates to an in vitro method of inducing terminal differentiation of tumor cells in a tumor comprising contacting the cells with an effective amount of any one or more of the hydroxamic acid compounds described herein.

The methods of the instant invention can be practiced in vitro. It is also contemplated that the methods of selectively inducing terminal differentiation, cell growth arrest and/or apoptosis of neoplastic cells, and of inhibiting HDAC will comprise contacting the cells in vivo, i.e., by administering the compounds to a subject harboring neoplastic cells or tumor cells in need of treatment.

Thus, the present invention provides in vivo methods for selectively inducing terminal differentiation, cell growth arrest and/or apoptosis of neoplastic cells in a subject, thereby inhibiting proliferation of such cells in the subject, by administering to the subject an effective amount of any one or more of the hydroxamic acid derivatives described herein.

In a particular embodiment, the present invention relates to a method of selectively inducing terminal differentiation of neoplastic cells and thereby inhibiting proliferation of such cells in a subject. The method comprises administering to the subject an effective amount of one or more of the hydroxamic acid derivatives described herein.

In another embodiment, the invention relates to a method of selectively inducing cell growth arrest of neoplastic cells and thereby inhibiting proliferation of such cells in a subject. The method comprises administering to the subject an effective amount of one or more of the hydroxamic acid derivatives described herein.

In another embodiment, the invention relates to a method of selectively inducing apoptosis of neoplastic cells and thereby inhibiting proliferation of such cells in a subject. The method comprises administering to the subject an effective amount of one or more of the hydroxamic acid derivatives described herein.

In another embodiment, the invention relates to a method of treating a patient having a tumor characterized by proliferation of neoplastic cells. The method comprises administering to the patient one or more of the hydroxamic acid derivatives described herein. The amount of compound is effective to selectively induce terminal differentiation, induce cell growth arrest and/or induce apoptosis of such neoplastic cells and thereby inhibit their proliferation.

EXAMPLES

Examples provided are intended to assist in a further understanding of the invention. Particular materials employed, species and conditions are intended to be illustrative of the invention and not limiting of the reasonable scope thereof.

Example 1
Synthesis
The compounds of the present invention can be synthesized as exemplified in Schemes 1-4, which illustrate the synthesis of iminodiacetic-acid derived tertiary amine hydroxamic acids (compounds of Formulas II and III). Similar methodologies known to a person skilled in the art can be used to prepare the diamine compounds of Formulas IV and V.
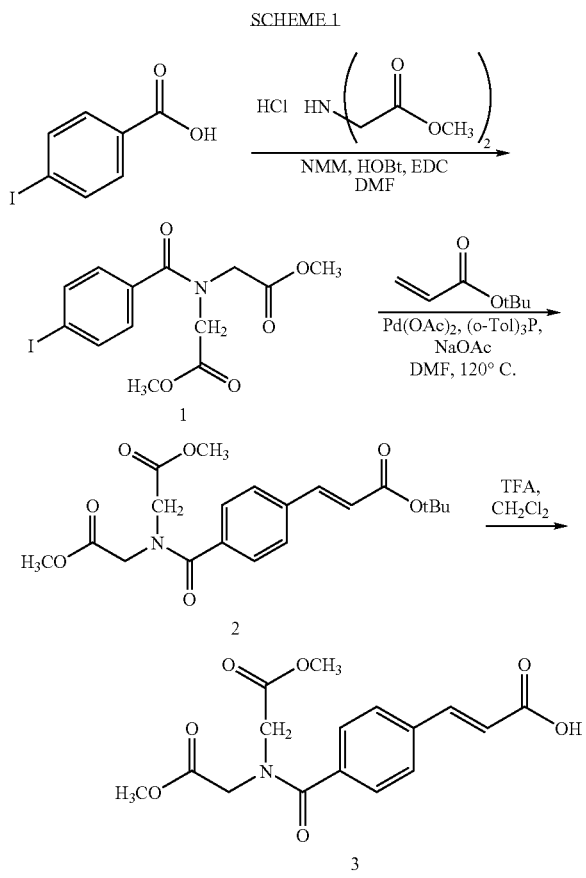
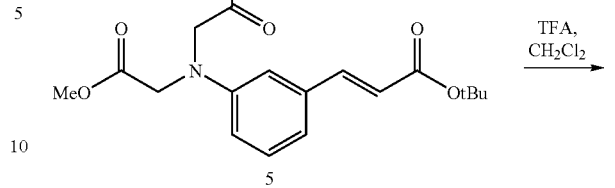
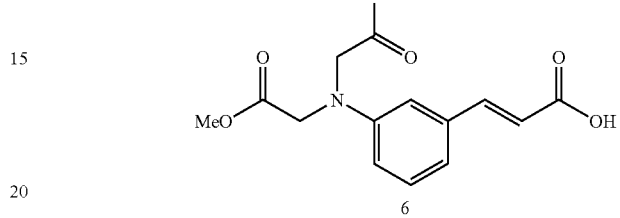
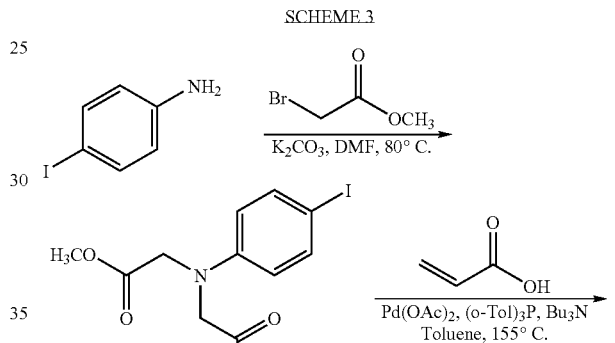
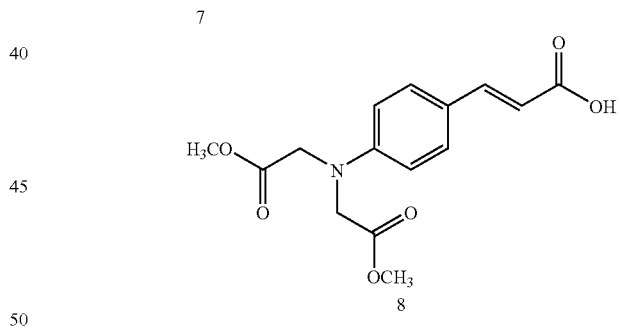
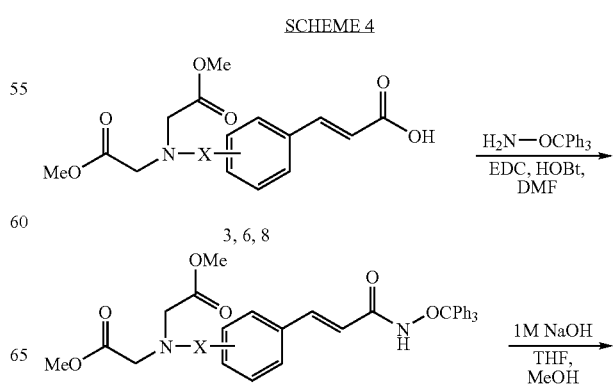

-continued
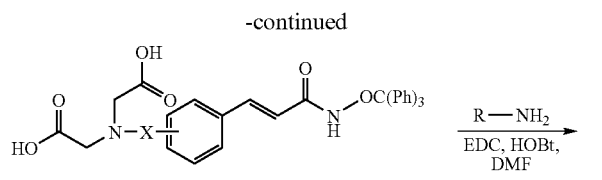
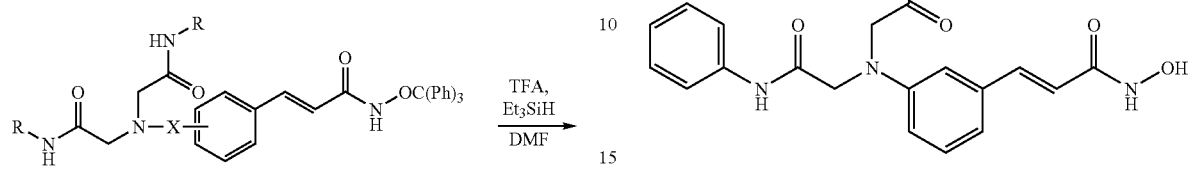
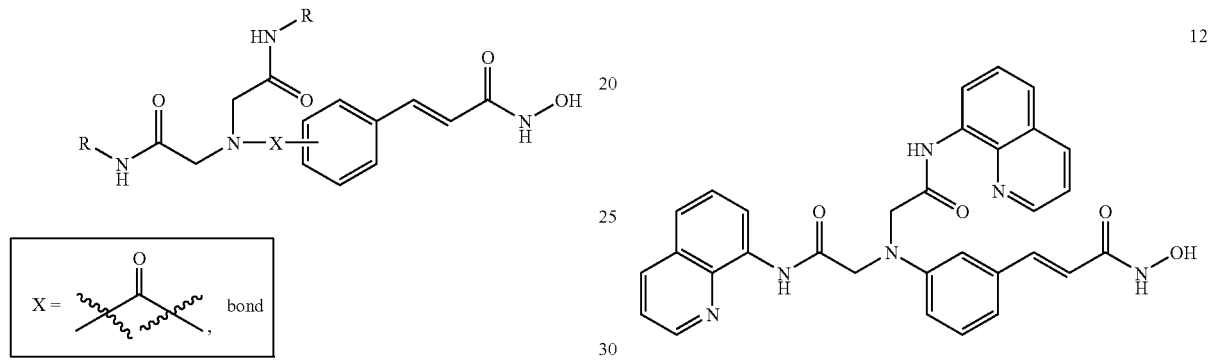
An exemplary non-limiting list of compounds synthesized in accordance with the above-procedures are presented below.
9
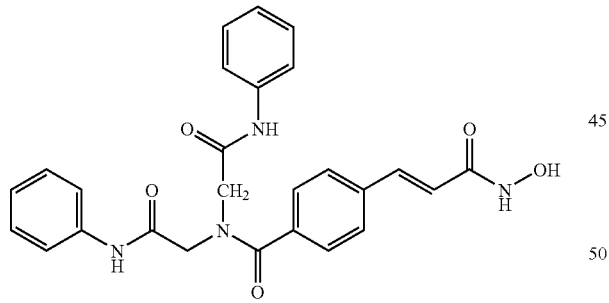
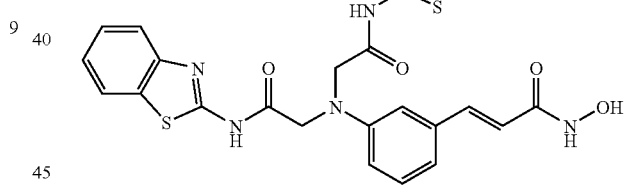
10
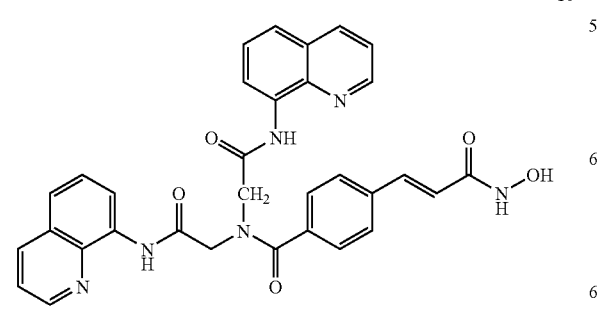
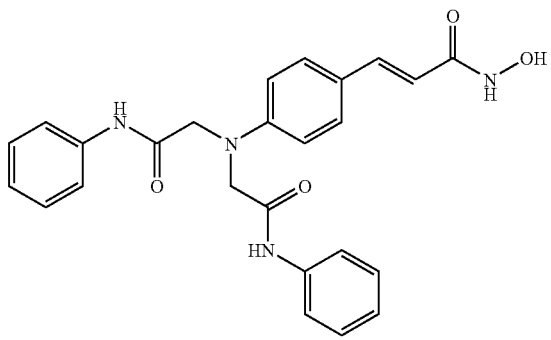

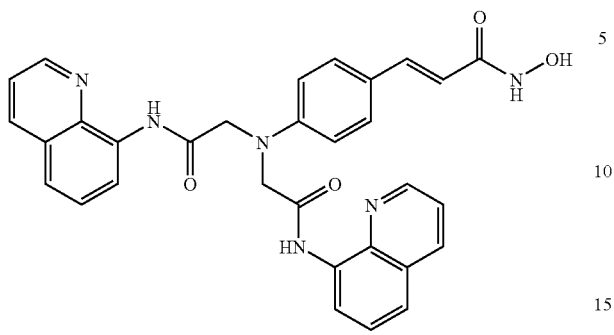

Comp. 9: 4-(2-Hydroxycarbamoyl-vinyl)-N,N-bis-phenyl-carbamoylmethyl-benzamide;
Comp. 10: 4-(2-Hydroxycarbamoyl-vinyl)-N,N-bis-(quinolin-8-ylcarbamoylmethyl)-benzamide;
Comp. 11: 3-[3-(Bis-phenylcarbamoylmethyl-amino)-phenyl]-N-hydroxy-acrylamide;
Comp. 12: 3-{3-[Bis-(quinolin-8-ylcarbamoylmethyl)-amino]-phenyl}-N-hydroxy-acrylamide;
Comp. 13: 3-{3-[Bis-(benzothiazol-2-ylcarbamoylmethyl)-amino]-phenyl}-N-hydroxy-acrylamide;
Comp. 14: 3-[4-(Bis-phenylcarbamoylmethyl-amino)-phenyl]-N-hydroxy-acrylamide; and
Comp. 15: 3-{4-[Bis-(quinolin-8-ylcarbamoylmethyl)-amino]-phenyl}-N-hydroxy-acrylamide.

Procedures:

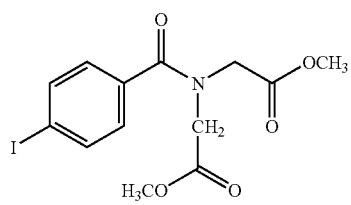

[(4-Iodo-benzoyl)-methoxycarbonylmethyl-amino]-acetic acid methyl ester (1)

Iminodiacetic dimethyl ester hydrochloride (624 mg, 3.24 mmol) was suspended in 5 mL of anhydrous DMF under nitrogen, and N-methylmorpholine (360 µL, 3.27 mmol) was added. After 5 minutes, 4-iodobenzoic acid (805 mg, 3.25 mmol) was added, followed by HOBt (450 mg, 3.33 mmol) and EDC (1.0 g, 5.28 mmol). The reaction was stirred overnight at 45° C. The solvent was removed and the residue was dissolved in EtOAc (20 mL) and washed with 0.5 M HCl, sat. NaHCO$_3$ and water. The organic phase was collected, the solvent removed and the mixture purified by column chromatography (silica; hexanes:EtOAc 90:10-65:45), yielding the product as a white solid. MS (ES+): Cal'd. 392.00 (MH$^+$), exp. 391.98 (MH$^+$).

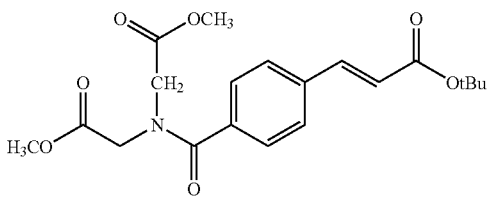

3-[4-(Bis-methoxycarbonylmethyl-carbamoyl)-phenyl]-acrylic acid tert-butyl ester (2)

The starting iodoamide (871 mg, 2.23 mmol) was dissolved in 10 mL of anhydrous DMF, followed by tert-butyl acrylate (1 mL, 6.73 mmol), sodium acetate (550 mg, 6.70 mmol), tri-o-tolylphosphine (81 mg, 0.266 mmol) and palladium (11) acetate (20 mg, 0.089 mmol). The reaction was stirred for 16 h at 115-120° C. The product was precipitated by addition of water and reprecipitated from methanol: water. MS (ES+): Cal'd. 392.43 (MH$^+$), exp. 392.13 (MH$^+$).

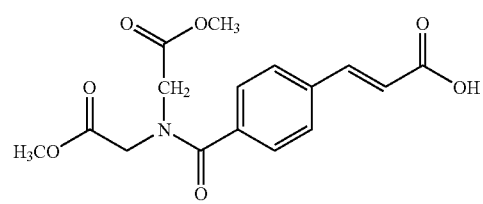

3-[4-(Bis-methoxycarbonylmethyl-carbamoyl)-phenyl]-acrylic acid (3)

The starting tert-butyl ester (769 mg, 1.96 mmol) was dissolved in 4.5 mL of anhydrous methylene chloride and treated with 1.5 mL of TFA for 16 h. The solvent was removed under reduced pressure and the residue was treated with water (5 mL) and sat. NaHCO$_3$. The resulting solution was acidified to pH 3 by addition of 5% citric acid, The product was extracted into EtOAc. The organic phase was collected, dried, and the solvent was removed under reduced pressure leaving the product as a solid. $^1$H NMR (DMSO-d$_6$, 200 MHz) 7.77 (d, J=8.0 Hz, 2H), 7.60 (d, J=16 Hz, 1H), 7.33 (d, J=8.0 Hz, 2H), 6.59 (d, J=16.2 Hz, 1H), 4.24 (s, 2H), 4.13 (s, 2H), 3.67 (s, 3H), 3.63 (s, 3H). MS (ES+): Cal'd. 336.11 (MH$^+$), exp. 336.11 (MH$^+$).

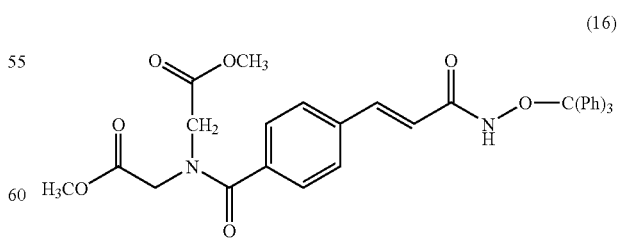

(16)

To a solution of the starting free acid (225 mg, 0.67 mmol) in 2.5 mL of anhydrous DMF was added HOBt (100 mg, 0.74 mmol), O-tritylhydroxylamine, and EDC. The reaction was stirred at room temperature overnight (16 h). The solvent was removed under reduced pressure and the residue was dissolved in the minimum amount of methylene chloride and purified by column chromatography (silica; hexanes:EtOAc 100:0-50:50). MS (ES+): Cal'd. 593.23 (MH+), exp. 593.24 (MH+).

(17)

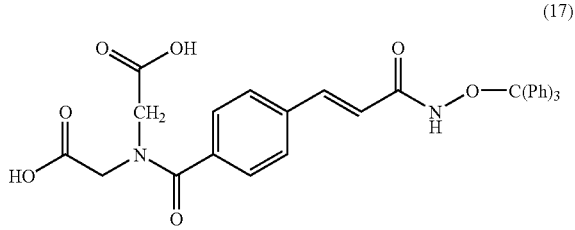

To a solution of the starting dimethyl ester (179 mg, 0.302 mmol) in 4 mL of THF was added 1 M aq. NaOH (1.5 mL) and enough methanol (0.1 mL) to obtain an homogeneous solution. The reaction was stirred at room temperature overnight (16 h). The reaction was diluted by addition of water (10 mL), and the pH was brought to 3 by addition of 5% citric acid. The product was extracted into EtOAc (2×20 mL). The organic phase was collected, dried (MgSO$_4$), and the solvent was removed under reduced pressure leaving the product as a white solid. This solid was dissolved in anhydrous DMF and brought directly to the next step. MS (ES–): Cal'd. 563.18 (MH+), exp. 563.63 (MH+).

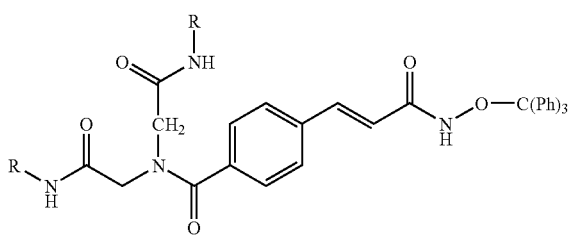

To a solution of the starting free diacid (0.15 mmol, crude from previous reaction) and HOBt (41 mg, 0.30 mmol) in 2 mL of anhydrous DMF was added aniline (65 μL, 0.70 mmol) or 8-aminoquinoline (70 mg, 0.49 mmol), followed by EDC (90 mg, 0.47 mmol). The reactions were stirred at room temperature overnight (16 h). The solvent was removed under reduced pressure and the residue was dissolved in EtOAc (20 mL) and washed with 0.5 M HCl, sat. NaHCO$_3$ and water. The organic phase was collected and dried (Mg SO$_4$) and the solvent removed. The residue was purified by column chromatography (silica; hexanes:EtOAc 90:10-0:100).

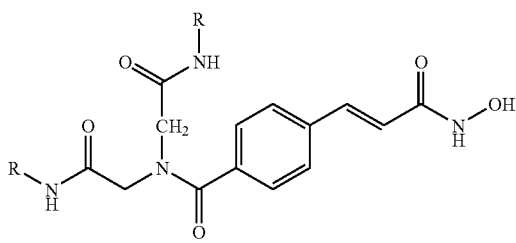

To a solution of the protected hydroxamic acid in 1 mL of methylene chloride was added TFA (50 μL). A deep yellow color developed immediately. The solution was let stand for 5 min. and then quenched by addition of triethylsilane. The solvent was reduced to 0.5 mL and diethyl ether (1-2 mL) was added. A precipitate formed. Sat. NaHCO$_3$ was added, and the suspension was shaken for 15 min. The solid was collected by filtration and washed with water and ether. The products were white powders.

Comp. 9: $^1$H NMR (DMSO-d$_6$, 200 MHz) 10.80 (s, 1H), 10.34 (s, 1H), 10.27 (s, 1H), 9.08 (s, 1H), 7.65-7.20 (m, 13H), 7.06 (t, J=7.0 Hz, 2M), 6.49 (d, J=16.8 Hz, 1H), 4.32 (s, 2H), 4.20 (s, 2H). MS (ES+): Cal'd. 473.18 (MH+), exp. 473.09 (MH+).

Comp. 10: $^1$H NMR (DMSO-d$_6$, 200 MHz) 10.82 (s, 1H), 10.42 (s, 1H), 8.90 (br d, J=19 Hz, 2H), 8.62 (m, 2H), 8.41 (t, J=7.2 Hz, 2H), 7.75-7.50 (m, 10H), 7.36 (d, J=15.8 Hz, 1H), 6.49 (d, J=15.8 Hz, 1H), 4.61 (s, 2H), 4.47 (s, 2H). MS (ES+): Cal'd. 575.21 (MH+), exp. 575.19 (MH+).

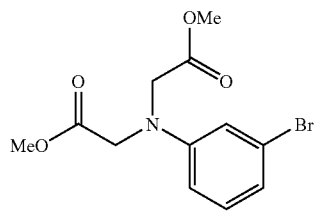

[(3-Bromo-phenyl)-methoxycarbonylmethyl-amino]-acetic acid methyl ester (4)

To a solution of 3-bromoaniline (1 mL, 9.18 mmol) in anhydrous DMF (15 mL) was added anhydrous potassium carbonate (1.5 g, 10.85 mmol) and methyl bromoacetate (2 mL, 21.8 mmol). The suspension was stirred at 80° C. for 2 days. The solvent was removed under reduced pressure and the residue was diluted with EtOAc (50 μL) and washed with sat. NaHCO$_3$ (20 mL), and water (20 mL). The organic phase was collected, dried (MgSO$_4$) and the solvent was removed. The product was purified by column chromatography (silica; hexanes:EtOAc 100:0-80:20). MS (ES+): Cal'd. 316.02 (MH+), exp. 316.06 (MH+).

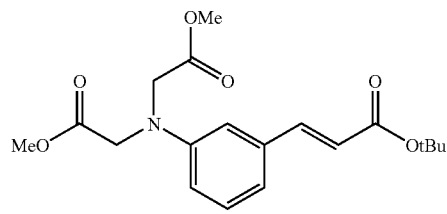

3-[3-(Bis-methoxycarbonylmethyl-amino)-phenyl]-acrylic acid tert-butyl ester (5)

The starting bromide (1.51 g, 4.78 mmol) was reacted with tert-butyl acrylate (1.20 mL, 8.08 mmol) in the presence of tri-o-tolylphosphine (87 mg, 0.286 mmol), palladium (II) acetate (21 mg, 0.094 mmol), and sodium acetate (1.17 g, 14.3 mmol) in 10 mL of anhydrous DMF at 120° C., as indicated for compound #2. The product was purified by column chromatography (silica; hexanes: EtOAc 90: 10-60: 40). MS (ES+): Cal'd. 364.18 (MH+), exp. 364.16 (MH+).

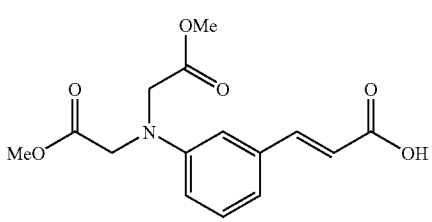

3-[3-(Bis-methoxycarbonylmethyl-amino)-phenyl]-acrylic acid (6)

A solution of the starting tert-butyl ester (735 mg, 2.02 mmol) in 4.5 mL of anhydrous methylene chloride was treated with 1.5 mL of TFA, using the same procedure reported for comp. #3. The title compound was obtained as a solid. $^1$H NMR (DMSO-$d_6$, 200 MHz) 7.49 (d, J=15.8 Hz, 1H), 7.19 (t, J=8.0 Hz, 1H), 6.99 (d, J=8.0 Hz, 1H), 6.87 (m, 1H), 6.59 (br d, J=8 Hz, 1H), 7.46 (d, J=15.8 Hz, 1H), 4.25 (s, 4H), 3.64 (s, 6H). MS (ES+): Cal'd. 308.12 (MH$^+$), exp. 308.10 (MH$^+$).

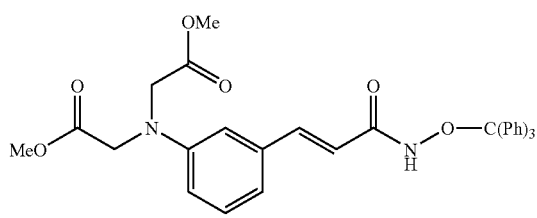

A solution of the starting free acid (240 mg, 0.78 mmol) in 2.5 mL of anhydrous DMF was treated with HOBt (100 mg, 0.74 mmol), O-tritylhydroxylamine (300 mg, 1.09 mmol) and EDC (225 mg, 1.17 mmol), using the same procedure reported for compound #16. The product was purified by column chromatography (silica; hexanes:EtOAc 100:0-50:50). MS (ES+): Cal'd. 565.24 (MH$^+$), exp. 565.25 (MH$^+$).

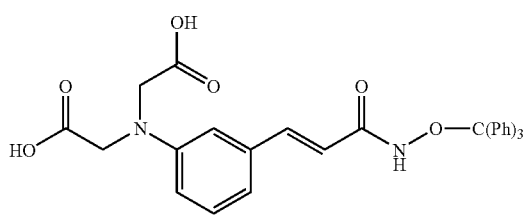

A solution of the starting dimethyl ester (250 mg, 0.443 mmol) in 4 mL of THF was treated as reported for compound #17. The product was obtained as a white solid. This solid was dissolved in anhydrous DMF and brought directly to the next step. MS (ES+): Cal'd. 537.20 (MH$^+$), exp. 537.01 (MH$^+$). MS (ES−): Cal'd. 535.19 (M-H$^+$), exp. 535.54 (M-H$^+$).

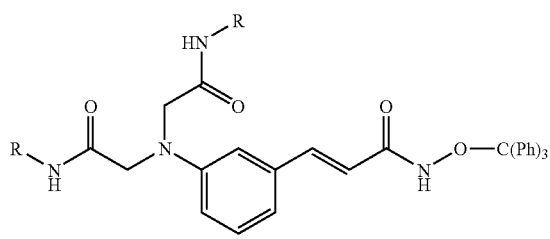

To a solution of the starting free diacid (0.15 mmol, crude from previous reaction) and HOBt (41 mg, 0.30 mmol) in 2 mL of anhydrous DMF was added aniline (70 μL, 0.75 mmol) or 8-aminoquinoline (67 mg, 0.47 mmol), or 2-aminobenzothiazole (67 mg, 0.45 mmol), followed by EDC (90 mg, 0.47 mmol). The reactions treated as indicated for the previous compounds and the products were isolated by column chromatography (silica; hexanes:EtOAc 90:10-0:100).

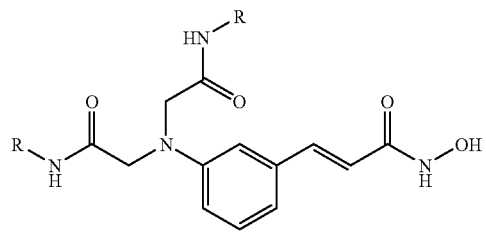

The protected hydroxamic acids were deprotected according to the procedure outlined above. The products were white powders.

Comp. 11: $^1$H NMR (DMSO-$d_6$, 200 MHz) 10.90 (s, 2H), 7.66 (d, J=8 Hz, 4H), 7.40-7.20 (m, 7H), 7.07 (m, 3H), 6.92 (d, J=7 Hz, 1H), 6.70 (s, 1H), 6.54 (br d, J=10 Hz, 1H), 6.35 (d, J=16.2 Hz, 1H), 4.38 (s, 4H). MS (ES+): Cal'd. 445.19 (MH$^+$), exp. 445.10 (MH$^+$).

Comp. 12: $^1$H NMR (DMSO-$d_6$, 200 MHz) 10.66 (s, 2H), 8.84 (dd, J1=4 Hz, J2=1.4 Hz, 2H), 8.65 (dd, J1=7.2 Hz, J2=1.6 Hz, 2H), 8.39 (dd, J1=8.4 Hz, J2=1.6 Hz, 2H), 7.70-7.50 (m, 6H), 7.37 (d, J=15.8 Hz, 1H), 7.23 (t, J=8 Hz, 1H), 7.10 (br s, 1H), 6.96-6.84 (m, 2H), 6.38 (d, J=16 Hz, 1H), 4.38 (s, 4H). MS (ES+): Cal'd. 547.21 (MH$^+$), exp. 547.21 (MH$^+$).

Comp. 13: $^1$H NMR (DMSO-$d_6$, 200 MHz) 10.65 (br s, 1H), 9.00 (br s, 1H), 7.96 (d, J=7.6 Hz, 2H), 7.74 (d, J=8.0 Hz, 2H), 7.46-7.38 (m, 2H), 7.32-7.19 (m, 4H), 6.92 (br d, J=7.0 Hz, 1H), 6.83 (s, 1H), 6.59 (br d, J=7.0 Hz, 1H), 6.37 (d, J=16.2 Hz, 1H), 4.53 (s, 4H). MS (ES+): Cal'd. 559.12 (MH$^+$), exp. 559.10 (MH$^+$).

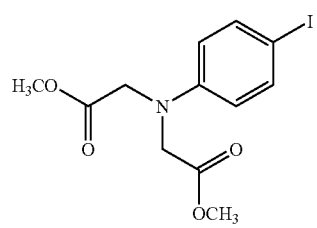

[(4-Iodo-phenyl)-methoxycarbonylmethyl-amino]-acetic acid methyl ester (7)

A solution of 4-iodoaniline (3.83 g, 17.5 mmol) in anhydrous DMF (20 mL) was reacted with methyl bromoacetate (6.43 g, 42.0 mmol) and anhydrous potassium carbonate (5.8 g, 42.0 mmol) 60° C. overnight. The solvent was removed under reduced pressure and the residue was diluted with EtOAc (50 mL) and washed with sat. NaHCO$_3$ (20 mL), and water (20 mL). The organic phase was collected, dried (MgSO$_4$) and the solvent was removed. The product was purified by column chromatography (silica; hexanes:EtOAc 100:0-80:20). MS (ES+): Cal'd. 364.01 (MH$^+$), exp. 364.01 (MH$^+$).

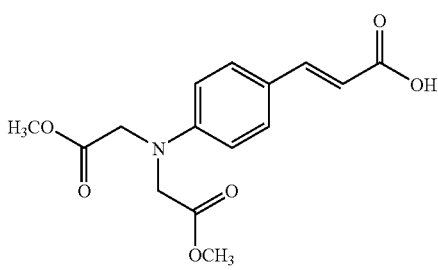

3-[4-(Bis-methoxycarbonylmethyl-amino)-phenyl]-acrylic acid (8)

The starting iodide (1.11 g, 3.06 mmol) was mixed with toluene (5 mL) and tributylamine (2 mL, 8.39 mmol). To this solution was added acrylic acid (320 μL, 4.67 mmol), tri-o-tolylphosphine (140 mg, 0.46 mmol) and palladium (II) acetate (34 mg, 0.151 mmol). The solution was stirred at 155° C. under nitrogen, until a black precipitate was observed (2 h). The solution was cooled to room temperature. The solvent was removed under high vacuum and the residue was dissolved in EtOAc (100 mL) and washed with 5% citric acid (2×50 mL) and water (50 mL). The organic phase was collected, dried (MgSO$_4$) and the solvent was removed. The residue was triturated with 5 mL of methylene chloride. The pale yellow solid was collected by filtration. This product was pure enough to be used in the next step. $^1$H NMR (DMSO-d$_6$, 200 MHz) 12.05 (br.s, 1H), 7.47 (t, J=8.4 Hz, 2H), 7.45 (d, J=16 Hz, 1H), 6.55 (d, J=8.6 Hz, 2H), 6.23 (d, J=15.8 Hz, 1H), 4.26 (s, 4H), 3.64 (s, 6H). MS (ES+): Cal'd. 308.12 (MH$^+$), exp. 308.12 (MH$^+$).

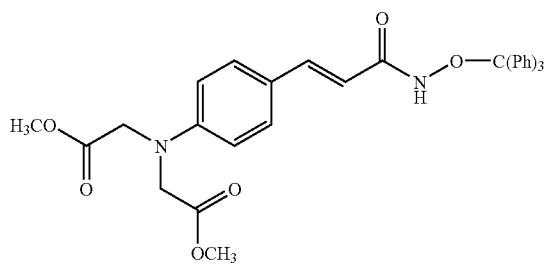

A solution of the starting free acid (420 mg, 1.37 mmol) in 10 mL of anhydrous DMF was treated with O-tritylhydroxylamine (610 mg, 2.22 mmol) and EDC (450 mg, 2.35 mmol), using the same procedure reported for compound #16. The product was purified by column chromatography (silica; hexanes:EtOAc 100:0-50:50).

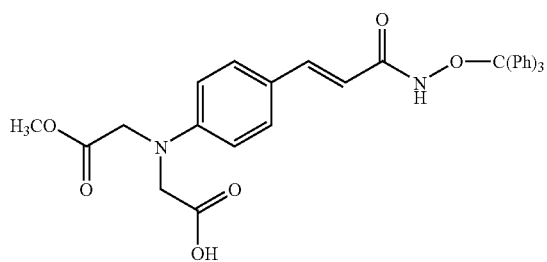

A solution of the starting dimethyl ester (124 mg, 0.22 mmol) in 3 mL of THF and 3 mL of MeOH was treated with 2 mL of 1M aq. NaOH for 2 h. The reaction volume was reduced by rotary evaporation and the aqueous residue was acidified (pH 3) by addition of 5% citric acid. The product was extracted into EtOAc (3×20 mL). The organic phase was collected, dried, and the solvent was removed under reduced pressure leaving the product as a white solid. This solid was dissolved in anhydrous DMF and brought directly to the next step.

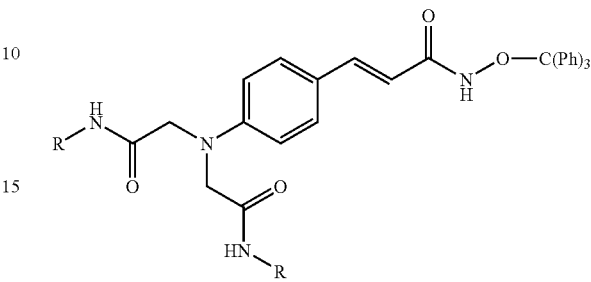

To a solution of the starting free diacid (0.12 mmol, crude from previous reaction) and HOBt (35 mg, 0.26 mmol) in 2 mL of anhydrous DMF was added aniline (40 μL, 0.43 mmol) or 8-aminoquinoline (60 mg, 0.42 mmol), followed by EDC (80 mg, 0.42 mmol). The reactions were stirred at room temperature overnight (16 h). The product were precipitated by addition of water (3 mL) and collected by filtration. They were purified further by column chromatography (silica; hexanes:EtOAc 90:10-50:50).

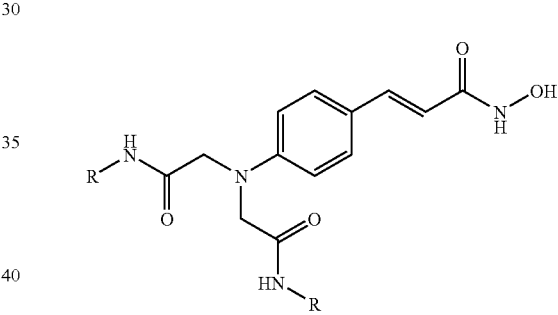

The protected hydroxamic acids were deprotected according to the procedure outlined above. The products were white powders.

Comp. 14: $^1$H NMR (DMSO-d$_6$, 200 MHz) 10.92 (br s, 1H), 7.65 (d, J=8.0 Hz, 4H), 7.46-7.20 (m, 6H), 7.08 (t, J=7.0 Hz, 2H), 6.56 (d, J=8.4 Hz, 2H), 6.17 (d, J=14.0 Hz, 1H), 4.39 (s, 4H). MS (ES+): Cal'd. 445.19 (MH$^+$), exp. 445.25 (MH$^+$).

Comp. 15: R=8-Quinolyl: MS(ES+): Cal'd. 547.21 (MH$^+$), exp. 547.27 (MH$^+$).

Example 2

HDAC Inhibition by Novel Compounds

HDAC1-Flag Assay:

Novel compounds were tested for their ability to inhibit histone deacetylase, subtype 1 (HDAC1) using an in vitro deacetylation assay. The enzyme source for this assay was an epitope-tagged human HDAC1 complex immuno-purified from stably expressing mammalian cells. The substrate consisted of a commercial product containing an acetylated lysine side chain (Biomol Research Laboratories, Inc., Plymouth Meeting, Pa.). Upon deacetylation of the substrate by incubation with the purified HDAC1 complex, a fluorophore is produced that is directly proportional to the level of deacetylation. Using a substrate concentration at the Km for the enzyme preparation, the deacetylation assay was performed in the presence of increasing concentrations of novel compounds to semi-quantitatively determine the concentration of compound required for 50% inhibition (IC50) of the deacetylation reaction.

Results:

The $IC_{50}$ values of the compounds described in Example 1 were determined according to the method set forth above. All of the compounds were able to inhibit 50% of the deacetylation reaction at a concentration below about 500 nM. Several of the compounds were able to inhibit 50% of the deacetylation reaction at a concentration below about 100 nM. Several of the compounds were able to inhibit 50% of the deacetylation reaction at a concentration below about 50 nM. Several of the compounds were able to inhibit 50% of the deacetylation reaction at a concentration below about 20 nM. Several compounds were able to inhibit 50% of the deacetylation reaction at a concentration range of about 15 and 20 nM. Several compounds were able to inhibit 50% of the deacetylation reaction at a concentration range of about 10 and 15 nM. Several compounds were able to inhibit 50% of the deacetylation reaction at a concentration range of about 5 and 10 nM. Several compounds were able to inhibit 50% of the deacetylation reaction at a concentration of below about 10 nM.

Example 3

HDAC Inhibition in Cell Lines

MTS Assay:

The novel compounds of the instant invention were tested for their ability to inhibit proliferation of the murine erythroleukemia cell line SC9.

The MTS assay, also referred to as the Cell Titer 96 Aqueous One Solution Cell Proliferation Assay, is a colorimetric method for determining the number of viable cells in proliferation, cytotoxicity or chemosensitivity assays. The MTS reagent contains a novel tetrazolium compound [3-(4,5-dimethylthiazol-2-yl)-5-(3-carboxymethoxyphenyl)-2-(4-sulfophenyl)-2H-tetrazolium, inner salt] and electron coupling reagent (phenazine ethosulfate; PES). Murine erythroleukemia cells (SC-9) were incubated with vehicle or increasing concentrations of compound for 48 hours. Cell proliferation was quantitated by adding a small amount of the MTS reagent directly to culture wells, incubating for 1-4 hours and then recording the absorbance at 490 nM with a 96-well plate reader. The quantity of formazan product, as measured by 490 nM absorbance, is directly proportional to the number of living cells in culture.

Results:

The results of the SC9-cell based MTS assay from a select group of novel compounds show that the compounds are able to inhibit cellular proliferation at a concentration below 5000 nM. Several of the compounds are able to inhibit cellular proliferation at a concentration below 1000 nM. Several of the compounds are able to inhibit cellular proliferation at a concentration range of about 500-1000 nM. Several other compounds are able to inhibit cellular proliferation at a concentration range of about 100-500 nM. Several other compounds are able to inhibit cellular proliferation at a concentration of below 100 nM. Several other compounds are able to inhibit cellular proliferation at a concentration range of about 50-100 nM. Several other compounds are able to inhibit cellular proliferation at a concentration of below 50 nM. Several other compounds are able to inhibit cellular proliferation at a concentration of below 25 nM. Several other compounds are able to inhibit cellular proliferation at a concentration of below 10 nM.

While this invention has been particularly shown and described with references to embodiments thereof, it will be understood by those skilled in the art that various changes in form and details may be made therein without departing from the meaning of the invention described. Rather, the scope of the invention is defined by the claims that follow.

What is claimed is:

1. A compound represented by the following structural formula:

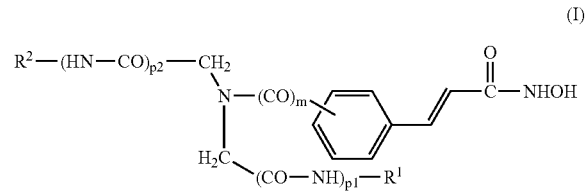

wherein
m is 0 or 1;
$p^1$ and $p^2$ are 1;
$R^1$ and $R^2$ are, independently of each other, unsubstituted or substituted and selected from hydrogen $C_1$-$C_{10}$ alkyl, $C_2$-$C_{10}$ alkenyl, cycloalkyl, aryl, heterocyclyl, heteroaryl, $C_1$-$C_{10}$ alkyl, $C_2$-$C_{10}$ alkenyl, $C_1$-$C_{10}$ alkylcycloalkyl, $C_1$-$C_{10}$ alkylaryl, $C_1$-$C_{10}$ alkylheterocyclyl and $C_1$-$C_{10}$ alkylheteroaryl; or
or a stereoisomer, enantiomer, racemate, or pharmaceutically acceptable salt thereof.

2. The compound according to claim 1, wherein $R^1$ and $R^2$ are, independently of each other, unsubstituted or substituted with one, two or three substitutents selected from $R^{sub}$;
wherein
$R^{sub}$ is independently selected from $C_1$-$C_{10}$ alkyl, $C_1$-$C_{10}$ haloalkyl, $C_2$-$C_{10}$alkenyl, cycloalkyl, aryl, heterocyclyl, heteroaryl, $C_1$-$C_{10}$ alkyl-$C_2$-$C_{10}$alkenyl, $C_1$-$C_{10}$ alkylcycloalkyl, $C_1$-$C_{10}$ alkylaryl, $C_1$-$C_{10}$ alkylheterocyclyl, $C_1$-$C_{10}$ alkylheteroaryl, halogen, hydroxy, $C_1$-$C_{10}$ alkyloxy, $C_1$-$C_{10}$ haloalkyloxy, aryloxy, nitro, oxo, —CN, —C(=O)H, —C(=O)OH, amino, N-$C_1$-$C_{10}$ alkylamino, N,N-di $C_1$-$C_{10}$ alkylamino, N-arylamino, N,N-diarylamino, N-$C_1$-$C_{10}$ alkyl-N-arylamino, azido, and C(=O)OR wherein R is aryl or $C_1$-$C_{10}$ alkyl.

3. The compound according to claim 1, wherein $R_1$ and $R_2$ are, independently of each other, unsubstituted or substituted and selected from phenyl, naphthyl, fluorenyl, biphenyl, benzyl, —$CH_2CH_2Ph$, —$CH_2CH_2CH_2Ph$, cyclopropyl, cyclohexyl, quinolinyl, isoquinolinyl, —$CH_2$-quinolinyl, —$CH_2$-isoquinolinyl, thiazolyl, benzothiazolyl, $CH(Ph)_2$ and $C_1$-$C_{10}$alkyl.

4. The compound according to claim 3, wherein $R^1$ and $R^2$ are, independently of each other, unsubstituted or substituted with one, two or three substitutents selected from $R^{sub}$;
wherein
$R^{sub}$ is independently selected from $C_1$-$C_4$ alkyl, $C_1$-$C_4$ haloalkyl, $C_1$-$C_4$ haloalkyloxy, $C_1$-$C_4$ alkyloxy, aryl, halogen and nitro.

5. The compound according to claim 1, represented by the structure of formula II:

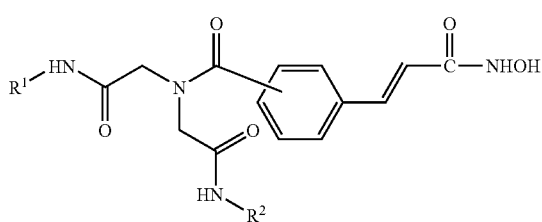
(II)

wherein $R^1$ and $R^2$ are as defined in claim 1;
or a stereoisomer, enantiomer, racemate, or pharmaceutically acceptable salt, thereof.

6. The compound according to claim 1, represented by the structure of formula III:

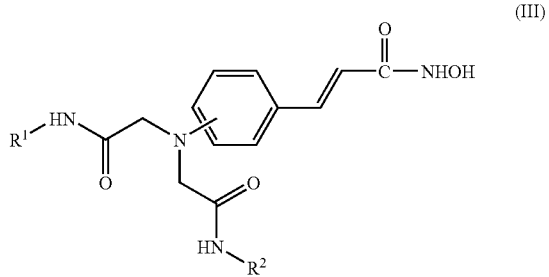
(III)

wherein $R^1$ and $R^2$ are as defined in claim 1; or a stereoisomer, enantiomer, racemate, or pharmaceutically acceptable salt thereof.

7. A pharmaceutical composition comprising a pharmaceutically effective amount of the compound according to claim 1, and a pharmaceutically acceptable carrier.

8. A method of treating cancer in a mammal comprising the step of administering a therapeutically effective amount of the compound according to claim 1 to the mammal.

9. A compound which is selected from:
   4-(2-Hydroxycarbamoyl-vinyl)-N,N-bis-phenylcarbamoylmethyl-benzamide;
   4-(2-Hydroxycarbamoyl-vinyl)-N,N-bis-(quinolin-8-ylcarbamoylmethyl)-benzamide;
   3-[3-(Bis-phenylcarbamoylmethyl-amino)-phenyl]-N-hydroxy-acrylamide;
   3-{3-[Bis-(quinolin-8-ylcarbamoylmethyl)-amino]-phenyl}-N-hydroxy-acrylamide;
   3-{3-[Bis-(benzothiazol-2-ylcarbamoylmethyl)-amino]-phenyl}-N-hydroxy-acrylamide;
   3-[4-(Bis-phenylcarbamoylmethyl-amino)-phenyl]-N-hydroxy-acrylamide; and
   3-{4-[Bis-(quinolin-8-ylcarbamoylmethyl)-amino]-phenyl}-N-hydroxy-acrylamide;
   or a stereoisomer, enantiomer, racemate, or pharmaceutically acceptable salt thereof.

10. A pharmaceutical composition comprising a pharmaceutically effective amount of the compound according to claim 9, and a pharmaceutically acceptable carrier.

11. A method of treating cancer in a mammal comprising the step of administering a therapeutically effective amount of the compound according to claim 9 to the mammal.

* * * * *